US012167848B2

(12) United States Patent
Krasniak et al.

(10) Patent No.: US 12,167,848 B2
(45) Date of Patent: Dec. 17, 2024

(54) BONE ANCHOR DELIVERY SYSTEM

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Carolyn Marie Krasniak, Melrose, MA (US); Cori Grace Pierce, Salem, NH (US)

(73) Assignees: Smith & Nephew, Inc.; Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 0 days.

(21) Appl. No.: 18/106,148

(22) Filed: Feb. 6, 2023

(65) Prior Publication Data

US 2023/0181186 A1    Jun. 15, 2023

Related U.S. Application Data

(63) Continuation of application No. PCT/US2021/049624, filed on Sep. 9, 2021.

(60) Provisional application No. 63/076,800, filed on Sep. 10, 2020.

(51) Int. Cl.
| | | |
|---|---|---|
| *A61B 17/068* | (2006.01) | |
| *A61B 17/064* | (2006.01) | |
| *A61B 17/04* | (2006.01) | |
| *A61B 17/072* | (2006.01) | |

(52) U.S. Cl.
CPC ........ *A61B 17/068* (2013.01); *A61B 17/0642* (2013.01); *A61B 17/0401* (2013.01); *A61B 17/0682* (2013.01); *A61B 17/072* (2013.01)

(58) Field of Classification Search
CPC ..... A61B 17/068; A61B 17/072; A61B 17/04; A61B 17/0401; A61B 17/0487; A61B 17/06; A61B 17/0642; A61B 17/0682; A61B 17/064; A61B 17/10
USPC ..... 227/19, 175.1, 902; 606/1, 99, 219, 221, 606/232
See application file for complete search history.

(56) References Cited

U.S. PATENT DOCUMENTS

| | | |
|---|---|---|
| 4,060,089 A | 11/1977 | Noiles |
| 4,994,073 A | 2/1991 | Green |
| 5,643,319 A * | 7/1997 | Green .................... A61B 17/06 606/221 |
| 6,179,840 B1 | 1/2001 | Bowman |
| 6,190,401 B1 | 2/2001 | Green et al. |
| 6,364,884 B1 | 4/2002 | Bowman et al. |
| 6,402,766 B2 | 6/2002 | Bowman et al. |
| 6,423,073 B2 | 7/2002 | Bowman |
| 6,436,110 B2 | 8/2002 | Bowman et al. |
| 6,447,517 B1 | 9/2002 | Bowman |

(Continued)

*Primary Examiner* — Scott A Smith
(74) *Attorney, Agent, or Firm* — Seager, Tufte & Wickhem LLP

(57) ABSTRACT

A delivery system for delivering an anchor member to a bone of a patient may include a bone punch including an elongate shaft, a head at a proximal end of the elongate shaft, and a piercing tip at a distal end of the elongate shaft. The piercing tip may be configured to be driven into the bone. An anchor member may be disposed over at least a portion of the piercing tip with the piercing tip extending distal of the anchor member. The anchor member may be configured to penetrate the bone of the patient in cooperation with the piercing tip.

19 Claims, 32 Drawing Sheets

(56) References Cited

U.S. PATENT DOCUMENTS

| | | |
|---|---|---|
| 6,497,707 B1 | 12/2002 | Bowman et al. |
| 6,656,183 B2 | 12/2003 | Colleran et al. |
| 7,214,232 B2 | 5/2007 | Bowman et al. |
| 8,016,867 B2 | 9/2011 | Bowman |
| 8,449,561 B2 | 5/2013 | Bowman |
| 8,506,591 B2 | 8/2013 | Danielson et al. |
| 8,702,718 B2 | 4/2014 | Bhatnagar et al. |
| 8,763,878 B2 | 7/2014 | Euteneuer et al. |
| 8,821,536 B2 | 9/2014 | Euteneuer et al. |
| 8,840,642 B2 | 9/2014 | Euteneuer et al. |
| 9,033,201 B2 | 5/2015 | Euteneuer |
| 9,247,978 B2 | 2/2016 | Euteneuer et al. |
| 9,271,726 B2 * | 3/2016 | Euteneuer ............... A61B 17/17 |
| 9,402,621 B2 | 8/2016 | Stone et al. |
| 9,566,063 B2 | 2/2017 | Euteneuer et al. |
| 9,855,037 B2 | 1/2018 | Euteneuer et al. |
| 9,955,968 B2 | 5/2018 | Euteneuer |
| 9,993,247 B2 * | 6/2018 | Euteneuer .......... A61B 17/0682 |
| 10,123,796 B2 | 11/2018 | Westling et al. |
| 10,383,624 B2 | 8/2019 | Gittings et al. |
| 10,758,228 B2 * | 9/2020 | Zenz-Olson .......... A61F 2/0811 |
| 11,076,851 B2 * | 8/2021 | Westling ............. A61B 17/0682 |
| 11,357,497 B1 * | 6/2022 | Anakwenze .......... A61F 2/0811 |
| 11,413,032 B2 * | 8/2022 | Running ............. A61B 17/0401 |
| 2008/0275469 A1 * | 11/2008 | Fanton ................ A61B 17/0487 606/232 |
| 2010/0121355 A1 | 5/2010 | Gittings et al. |
| 2010/0312250 A1 * | 12/2010 | Euteneuer .......... A61B 17/0642 606/99 |
| 2013/0245682 A1 * | 9/2013 | Euteneuer .......... A61B 17/0682 606/219 |
| 2015/0320413 A1 * | 11/2015 | Gittings ............. A61B 17/0401 606/232 |
| 2016/0120538 A1 | 5/2016 | Westling et al. |
| 2016/0120542 A1 * | 5/2016 | Westling ............. A61B 17/0642 227/175.1 |

\* cited by examiner

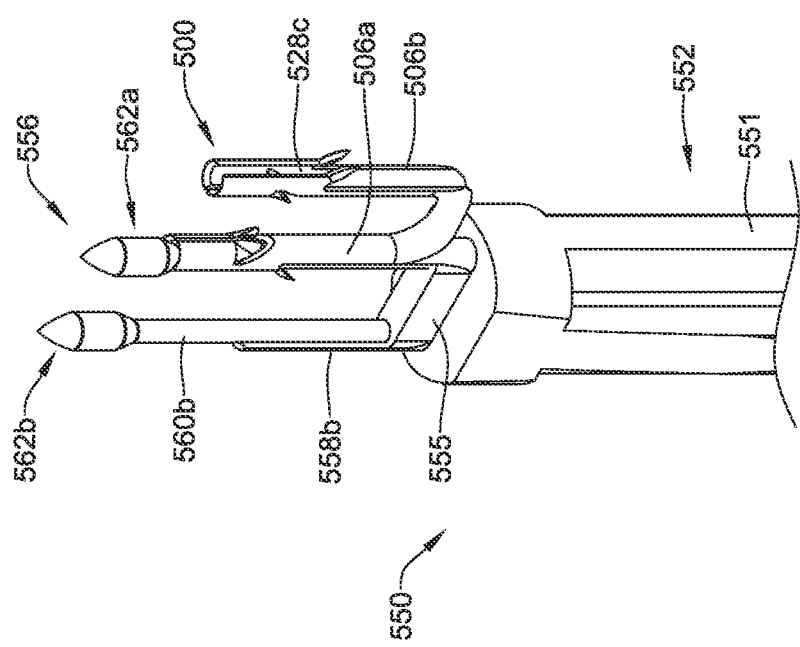

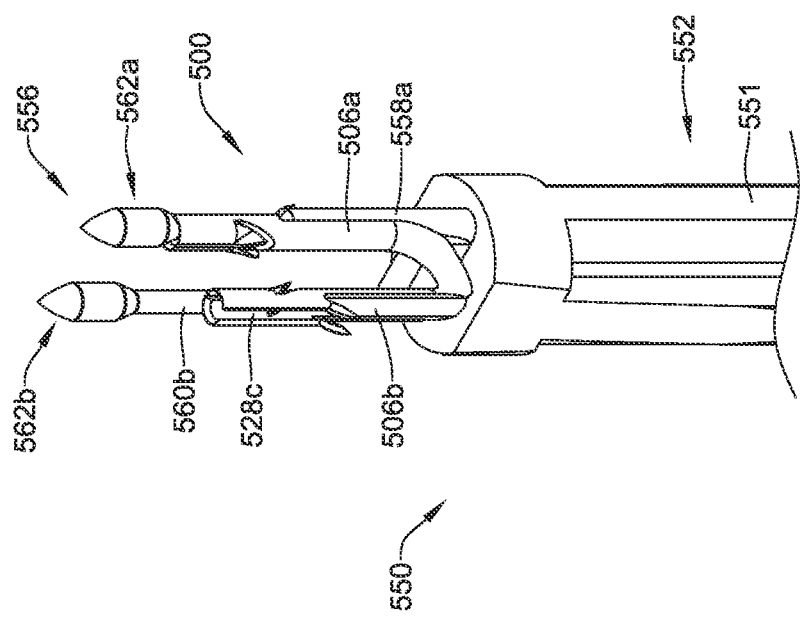

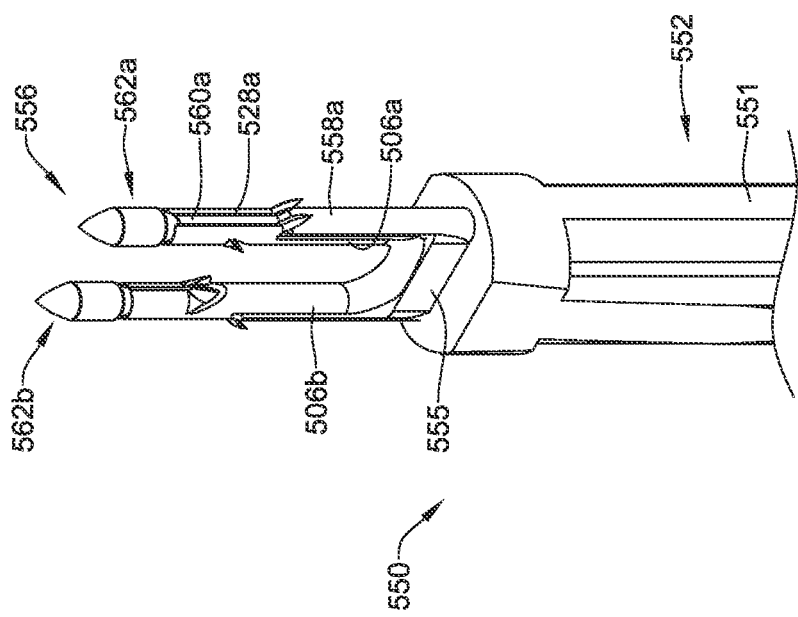

BONE ANCHOR DELIVERY SYSTEM

CROSS REFERENCE TO RELATED APPLICATIONS

This application is a continuation of International Application Serial No. PCT/US2021/049624, filed Sep. 9, 2021, titled BONE ANCHOR DELIVERY SYSTEM, which claims the benefit of and priority to U.S. Provisional Patent Application Ser. No. 63/076,800, filed on Sep. 10, 2020, titled BONE ANCHOR DELIVERY SYSTEM, the disclosures of which are incorporated herein by reference.

TECHNICAL FIELD

The present disclosure pertains generally to medical devices, and methods for manufacturing and/or using medical devices. More particularly, the present disclosure pertains to devices for making an aperture in bone within patients and delivering an anchor within the aperture, and methods for manufacturing and using such devices

BACKGROUND

Injuries may require the placement of anchors and/or implants into the bone(s) of a patient to repair. In one example, injuries to tendons may be treated by affixing a tendon repair implant to one or more bones associated with an articulating joint, such as the glenohumeral joint. Such affixation may use an anchor member, such as a staple, or other securement element inserted at least partially into bone, and in some cases, inserted at least partially into holes formed in the bone to receive the anchor member, staple, or other securement element. Formation of these holes and subsequent removal of a tool for doing so may be difficult due to the cortical elasticity of the bone. Of the known medical devices, and methods of manufacturing and using those devices, each has certain advantages and disadvantages. There is an ongoing need for improved and/or alternative medical devices and methods of making and using such devices.

SUMMARY

The disclosure provides design, material, manufacturing method, and use alternatives for medical devices.

An example is a delivery system for delivering an anchor member to a bone of a patient. The system includes a bone punch including an elongate shaft, a head at a proximal end of the elongate shaft, and a piercing tip at a distal end of the elongate shaft. Then the piercing tip is configured to be driven into the bone. An anchor member is disposed over at least a portion of the piercing tip with the piercing tip extending distal of the anchor member. The anchor member is configured to penetrate the bone of the patient in cooperation with the piercing tip.

Alternatively or additionally to any of the embodiments above, the piercing tip includes a first piercing element and a second piercing element extending parallel to the first piercing element.

Alternatively or additionally to any of the embodiments above, a distal end of the piercing tip includes an enlarged region having a diameter greater than a diameter of a proximal end region of the piercing tip extending proximal of the enlarged region.

Alternatively or additionally to any of the embodiments above, the anchor member includes a staple having a first leg, a second leg, and a bridge portion extending between a proximal end of the first leg and a proximal end of the second leg.

Alternatively or additionally to any of the embodiments above, the first and second legs each define a lumen extending therethrough.

Alternatively or additionally to any of the embodiments above, a diameter of the lumen is less than the diameter of the enlarged region of the piercing tip.

Alternatively or additionally to any of the embodiments above, proximal retraction of the piercing tip relative to the anchor member is configured to radially deform a distal end region of the first leg and a distal end region of the second leg.

Alternatively or additionally to any of the embodiments above, the first leg comprises a first pair of slots extending proximally from a distal end thereof and the second leg comprises a second pair of slots extending proximally from a distal end thereof.

Alternatively or additionally to any of the embodiments above, the first leg includes a first slit extending distally from a proximal end thereof and the second leg includes a second slit extending distally from a proximal end thereof.

Alternatively or additionally to any of the embodiments above, a distal end of the first leg and a distal end of the second leg are each beveled.

Another example is a delivery system for delivering an anchor member to a bone of a patient. The system includes a bone punch including an elongate shaft, a head at a proximal end of the elongate shaft, and a piercing tip at a distal end of the elongate shaft. The piercing tip includes at least one piercing element having a sharpened distal end. A distal end region of the at least one piercing element has an enlarged region having an outer diameter greater than an outer diameter of a proximal end region of the at least one piercing element. An anchor member is slidably disposed over the at least one piercing element with the sharpened distal end extending distal of the anchor member. The anchor member is configured to penetrate the bone of the patient in cooperation with the piercing tip.

Alternatively or additionally to any of the embodiments above, proximal translation of the piercing tip is configured to deploy the anchor member from the piercing tip.

Alternatively or additionally to any of the embodiments above, as the anchor member is deployed, a distal end region of the anchor member is configured to radially expand.

Alternatively or additionally to any of the embodiments above, the anchor member includes at least one lumen, the at least one lumen having a diameter less than the outer diameter of the enlarged region of the at least one piercing element.

Another example is a method of assembling an anchor member with a bone punch.

The method includes advancing an anchor member onto a piercing tip from a proximal end of the piercing tip to form a first subassembly. Thereafter, a cap member is attached to a proximal end region of the piercing tip with the anchor member located distal of the cap member to form a second subassembly. Thereafter, the cap member is attached to a distal end of an elongate shaft.

Alternatively or additionally to any of the embodiments above, advancing of the anchor member is limited by a mechanical interaction between an enlarged distal end region of the piercing tip and a distal end of the anchor member.

Alternatively or additionally to any of the embodiments above, the piercing tip extends through a lumen of the anchor member, wherein the lumen has a diameter less than a diameter of the enlarged distal end region of the piercing tip.

Alternatively or additionally to any of the embodiments above, the piercing tip has a sharpened tip located distal of the enlarged distal end region.

Alternatively or additionally to any of the embodiments above, the cap member includes at least one distally extending prong configured to extend axially along a portion of the piercing tip.

Alternatively or additionally to any of the embodiments above, the cap member includes at least one proximally extending arm configured to extend along an outer surface of the elongate shaft.

Another example is a method of assembling an anchor member with a bone punch. The method includes inserting a first piercing tip laterally into a lumen of a first leg of an anchor member in a direction generally perpendicular to a longitudinal axis of the first piercing tip. The anchor member is then rotated to align a second leg of the anchor member with a second piercing tip. Thereafter, a second piercing tip is inserted laterally into a lumen of a second leg of the anchor member in a direction generally perpendicular to a longitudinal axis of the second piercing tip.

Alternatively or additionally to any of the embodiments above, the first piercing tip has an enlarged distal end region located distal of the first leg and the second piercing tip has an enlarged distal end region located distal of the second leg.

Alternatively or additionally to any of the embodiments above, the enlarged distal end region of the first piercing tip has a diameter greater than a diameter of the lumen of the first leg, and the enlarged distal end region of the second piercing tip has a diameter greater than a diameter of the lumen of the second leg.

Alternatively or additionally to any of the embodiments above, the first leg includes a lateral slot extending an entire length of the lumen of the first leg opening laterally into the lumen of the first leg, and the second leg includes a lateral slot extending an entire length of the lumen of the second leg opening laterally into the lumen of the second leg.

Alternatively or additionally to any of the embodiments above, a width of the first slot is less than a diameter of a proximal portion of the first piercing tip extending proximal of the enlarged distal end region of the first piercing tip, and a width of the second slot is less than a diameter of a proximal portion of the second piercing tip extending proximal of the enlarged distal end region of the second piercing tip.

Alternatively or additionally to any of the embodiments above, the first piercing tip laterally snaps into the lumen of the first leg and the second piercing tip laterally snaps into the lumen of the second leg.

Another example is a bone staple. The bone staple includes a first leg, a second leg, and a bridge portion extending between a proximal end of the first leg and a proximal end of the second leg. The first and second legs each define a lumen extending therethrough.

Alternatively or additionally to any of the embodiments above, the first leg comprises a first pair of slots extending proximally from a distal end thereof and the second leg comprises a second pair of slots extending proximally from a distal end thereof.

Alternatively or additionally to any of the embodiments above, the first leg comprises a first slit extending distally from a proximal end thereof and the second leg comprises a second slit extending distally from a proximal end thereof.

Alternatively or additionally to any of the embodiments above, a distal end of the first leg and a distal end of the second leg are each beveled.

Alternatively or additionally to any of the embodiments above, a distal end region of the anchor member is configured to radially expand when deployed.

The above summary of some embodiments, aspects, and/or examples is not intended to describe each disclosed embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description in connection with the accompanying drawings, in which:

FIGS. 27-30 are perspective views illustrating another method of assembling the bone punch and anchor member delivery system with the anchor member of FIGS. 26A-26C.

Figure 1:
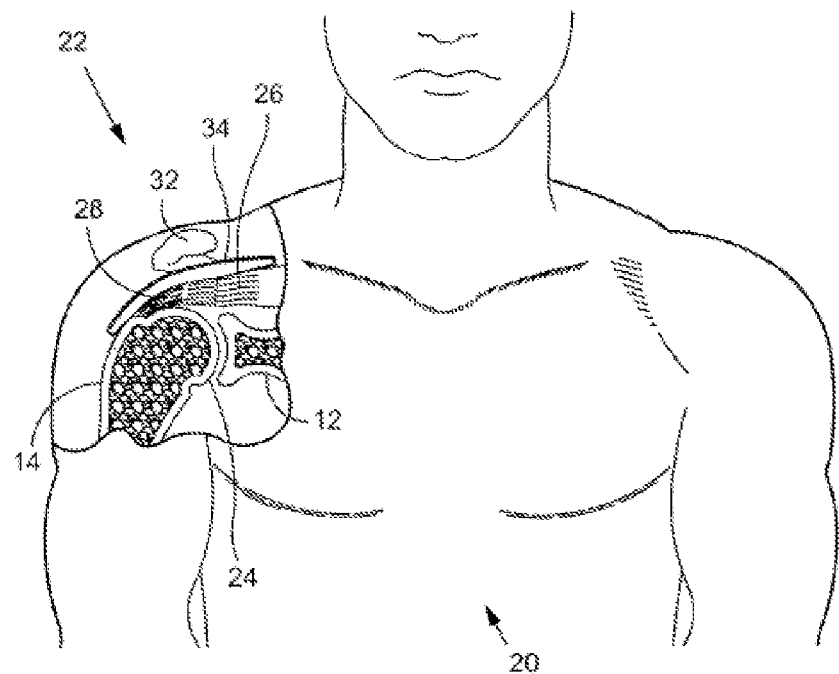
FIG. 1 is a stylized anterior view of a shoulder including a humerus and a scapula.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc. The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together, particularly where those discrete structures or elements remain individually identifiable.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures generally illustrate selected components and/or arrangements of medical devices or instruments. It should be noted that in any given figure, some features of the medical devices or instruments may not be shown, or may be shown schematically, for simplicity. Additional details regarding some of the elements of the medical devices or instruments may be illustrated in other figures in greater detail. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to features or elements may be equally referred to all instances and quantities beyond one of said feature or element. As such, it will be understood that the following discussion may apply equally to any and/or all of the elements for which there are more than one within the medical devices or instruments, unless explicitly stated to the contrary. Additionally, not all instances of some elements or features may be shown in each figure for clarity.

FIG. 1 is a stylized anterior view of a patient 20 illustrating one example area that may benefit from the disclosed invention. For purposes of illustration, a shoulder 22 of patient 20 is shown in partial cross-section in FIG. 1. The shoulder 22 includes a humerus 14 and a scapula 12. In FIG. 1, a head 24 of the humerus 14 can be seen mating with a glenoid fossa of the scapula 12 at a glenohumeral joint. With reference to FIG. 1, it will be appreciated that the glenoid fossa comprises a shallow depression in the scapula 12. Movement of the humerus 14 relative to the scapula 12 is controlled by a number of muscles including: the deltoid, the supraspinatus, the infraspinatus, the subscapularis, and the teres minor. For purposes of illustration, only the supraspinatus 26 is shown in FIG. 1.

In FIG. 1, a distal tendon 28 of the supraspinatus 26 meets the humerus 14 at an insertion point. The scapula 12 of the shoulder 22 includes an acromion 32. In FIG. 1, a subacromial bursa 34 is shown extending between the acromion 32 of the scapula 12 and the head 24 of the humerus 14. The subacromial bursa 34 is shown overlaying the supraspinatus 26 as well as the distal tendon 28 and a portion of the humerus 14. The subacromial bursa 34 is one of the hundreds of bursae found the human body. Each bursa comprises a fluid filled sac. The presence of these bursae in the body reduces friction between bodily tissues.

The exemplary anchors, staples, or fasteners described herein may be used to affix tendon repair implants to various target tissues in one example use of the disclosed medical device(s). The shoulder 22 depicted in FIG. 1 is one example where a tendon repair implant may be affixed to one or more bones associated with an articulating joint, such as the glenohumeral joint. Additionally, the tendon repair implant may be affixed to one or more tendons to be treated. In some cases, the tendons to be treated may be torn, partially torn, have internal micro-tears, be untorn, and/or be thinned due to age, injury or overuse.

Figure 2:
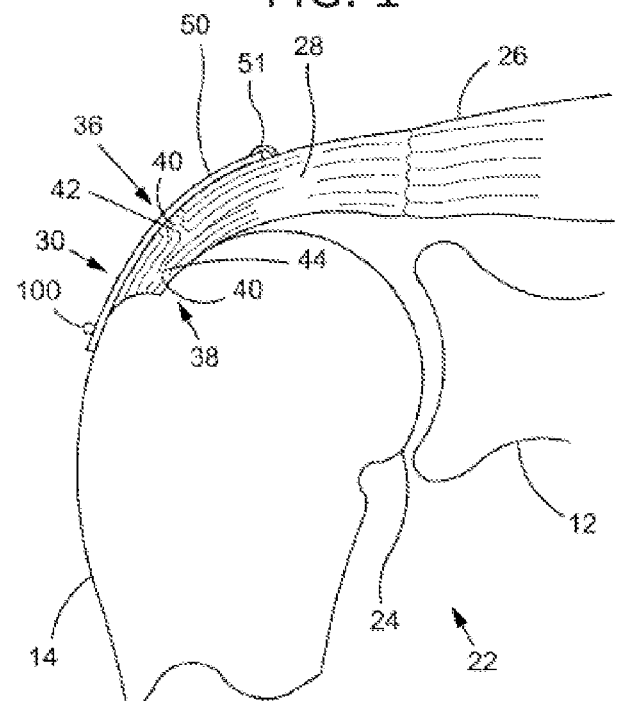
FIG. 2 is a stylized anterior view of a shoulder depicting the head of the humerus shown mating with the glenoid fossa of the scapula at a glenohumeral joint and a sheet-like material is affixed to the tendon.

FIG. 2 is a stylized anterior view of the shoulder 22 including the humerus 14 and the scapula 12. In FIG. 2, the head 24 of the humerus 14 is shown mating with the glenoid fossa of the scapula 12 at the glenohumeral joint. The supraspinatus 26 is also shown in FIG. 2. This muscle, along with others, controls the movement of the humerus 14 relative to the scapula 12. The distal tendon 28 of the supraspinatus 26 meets the humerus 14 at an insertion point 30.

As depicted in FIG. 2, the distal tendon 28 may include a first damaged portion 36. A number of loose tendon fibers 40 in the first damaged portion 36 are visible in FIG. 2. The first damaged portion 36 includes a first tear 42 extending partially through the distal tendon 28. The first tear 42 may therefore be referred to as a partial thickness tear. In FIG. 2, the first tear 42 begins on the side of the distal tendon 28 facing the subacromial bursa (e.g., FIG. 1) and ends midway through the distal tendon 28. Accordingly, the first tear 42 may be referred to as a bursal side tear.

In FIG. 2, the distal tendon 28 also includes a second damaged portion 38 located near insertion point 30. As illustrated, the second damaged portion 38 of the distal tendon 28 has become frayed and a number of loose tendon fibers 40 are visible. The second damaged portion 38 of the distal tendon 28 includes a second tear 44. The second tear 44 begins on the side of the distal tendon 28 facing the center of the head 24 of the humerus 14. Accordingly, the second damaged portion 38 may be referred to as an articular side tear.

FIG. 2 illustrates a sheet-like implant 50 has been placed over the bursal side of the distal tendon 28. The sheet-like implant 50 may be affixed to the distal tendon 28 by a plurality of tendon staples 51. The sheet-like implant 50 may be affixed to the humerus 14 by one or more bone staples 100, or other similar and/or suitable bone anchors. The sheet-like implant 50 extends over the insertion point 30, the first tear 42, and the second tear 44. Some methods in accordance with this disclosure may include placing a tendon repair implant on the bursal side of a tendon regardless of whether the tears being treated are on the bursal side, the articular side, or within the tendon. In some cases, the exact location and nature of the tears being treated may be unknown. In some cases, the tendon repair implant may be applied to the bursal side of the tendon to treat shoulder pain that is most likely caused by one or more partial thickness tears in the tendon.

Figure 3:
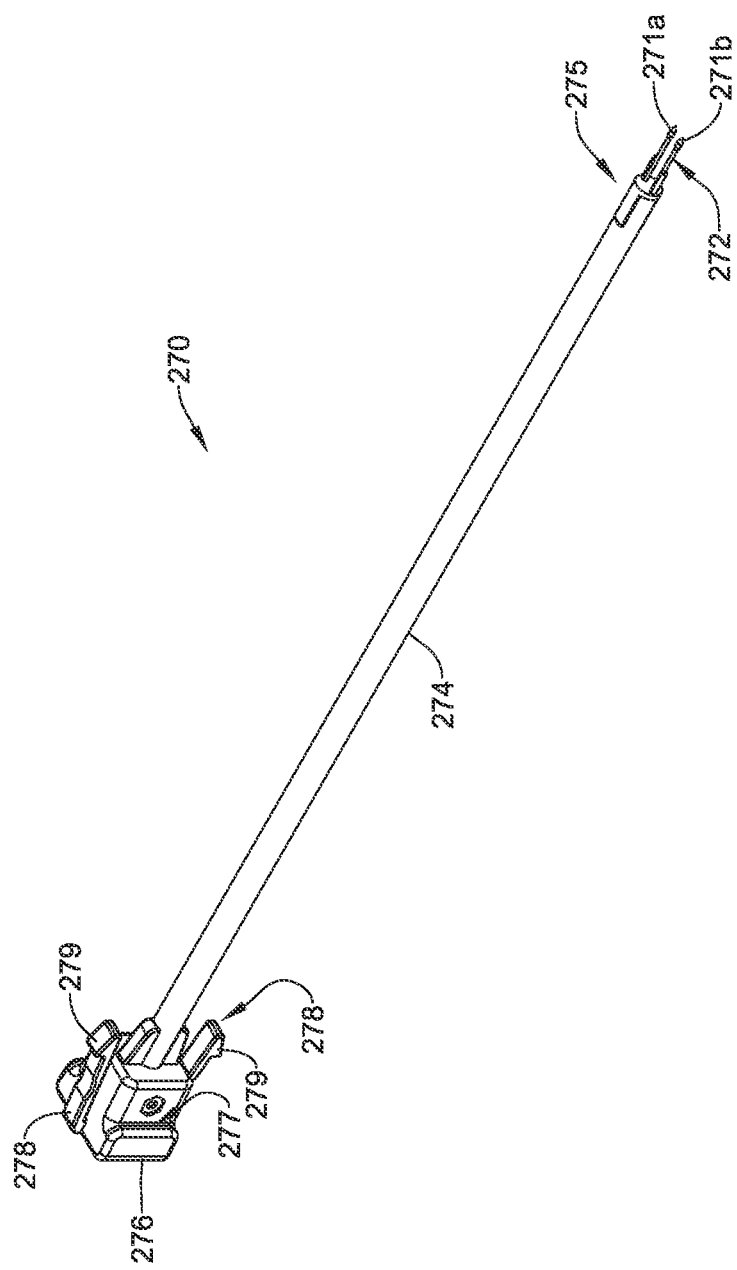
FIG. 3 is a perspective view illustrating aspects of an example bone punch and anchor member delivery system.

In some embodiments, a medical device may be used to form one or more holes within a bone (e.g., the humerus 14) of a patient to facilitate placement of the one or more bone staples 100 (or other anchor member) and/or to secure the sheet-like implant 50 to the bone. In some embodiments, the medical device (e.g., FIG. 4) may include a bone punch and anchor member delivery system 270 including an elongate shaft 274, a head 276 disposed at a proximal end of the elongate shaft 274, and a piercing tip 272 disposed at a distal end region 275 of the elongate shaft 274, as shown in FIG. 3 for example. In some embodiments, the bone punch and anchor member delivery system 270 may be configured to form one or more holes within the bone while delivering an anchor member 300 (see, for example, FIG. 12) in cooperation with or substantially simultaneously therewith. For example, the anchor member 300 may be loaded over or on the piercing tip 272 such that as the piercing tip enters the bone, the anchor member 300 is concurrently driven into the bone, as will be described in more detail herein.

In some embodiments, the bone punch and anchor member delivery system 270 and/or the piercing tip 272 may include a plurality of piercing tips, two or more piercing tips, a pair of piercing tips, etc. extending distally from the distal end region 275 of the elongate shaft 274. The piercing tip 272 may be configured to be driven into the bone (e.g., the humerus 14). In some embodiments, the piercing tip 272 may be a spike, a prong, a spear, or other suitable shape. As such, the piercing tip 272 may include a sharpened distal end and/or a tapered distal portion configured to engage and/or penetrate bone. In an example, the piercing tip 272 may include a first piercing element 271a and a second piercing element 271b extending parallel to the first piercing element 271a.

In some embodiments, the head 276 of the bone punch and anchor member delivery system 270 may include a plurality of connecting members 278. Each of the plurality of connecting members 278 may include an outwardly extending protrusion 279. In some embodiments, the plurality of connecting members 278 may be fixedly attached to opposing sides of the head 276. The plurality of connecting members 278 may extend from the head 276 distally toward the distal end region 275 of the elongate shaft 274. The plurality of connecting members 278 may extend laterally outward from the head 276 at an oblique angle to a longitudinal axis of the bone punch and anchor member delivery system 270 and/or the elongate shaft 274. In some embodiments, the plurality of connecting members 278 may be biased laterally outward from the head 276. Additional details regarding the plurality of connecting members 278 and their use will become apparent from the discussion herein.

In some embodiments, the head 276 may include one or more lateral projections. In some embodiments, the one or more lateral projections may be disposed between the plurality of connecting members 278 and/or between a proximal end of the head 276 and a distal end of the head 276. The one or more lateral projections may each and/or collectively define a distal surface 277 of the head 276. The distal surface 277 may be a distally facing surface and does not necessarily need to be a distalmost surface of the head 276. For example, the distal surface 277 may be disposed between the proximal end of the head 276 and the distal end of the head 276.

In some embodiments, the proximal end of the elongate shaft 274 may extend into the head 276 of the bone punch and anchor member delivery system 270. In some embodiments, the proximal end of the elongate shaft 274 may be fixedly attached to the head 276. In some embodiments, the elongate shaft 274 may be monolithically formed with the head 276, such as by casting, molding, or machining, for example. Other configurations are also contemplated. Similarly, a proximal end of the piercing tip 272 may extend into the distal end region 275 of the elongate shaft 274, as will be described in more detail herein. The proximal end of the piercing tip 272 may be fixedly attached to the elongate shaft 274. In some embodiments, the piercing tip 272 may be monolithically formed with the elongate shaft 274, such as by casting, molding, or machining, for example. Other configurations are also contemplated. Some examples of suitable but non-limiting materials for the bone punch and anchor member delivery system 270 and/or elements or components thereof are described below.

Figure 4:
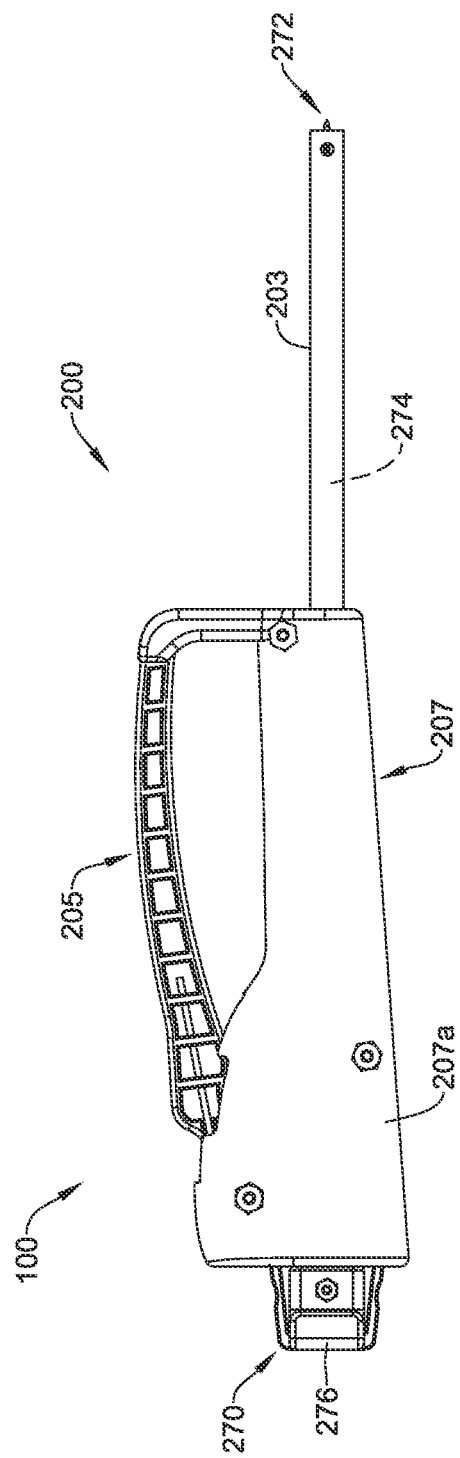
FIG. 4 is a side view illustrating aspects of an example medical device.

FIG. 4 illustrates aspects of a medical device 100 configured to form one or more holes within a bone of a patient and/or deliver an anchor member within the bone of the patient in a side view. The medical device 100 may comprise a handle assembly 200 including a housing 207, a lever 205 rotatably coupled to the housing 207, and a sheath 203 extending distally from the housing 207. In at least some embodiments, a proximal end of the sheath 203 may be fixedly attached to the housing 207. The sheath 203 may extend into and/or within the housing 207, such that the proximal end of the sheath 203 is disposed within a proximal portion of the housing 207, and the sheath 203 extends within the housing 207 and distally from a distal end of the housing 207. Some examples of suitable but non-limiting materials for the housing 207, the lever 205, the sheath 203, and/or elements or components thereof are described below.

The housing 207 may be formed as a multi-piece structure including a first housing portion 207a, seen in FIG. 4, and a second housing portion 207b, not visible in FIG. 4. For the purpose of illustration herein, one of the first housing portion 207a or the second housing portion 207b may be hidden from view in the figures to permit viewing of internal components and/or features thereof. The first housing portion 207a and the second housing portion 207b may be assembled together to form the housing 207. In the illustrated example(s), fasteners such as screws and nuts may be used to assemble the housing 207. However, other assembly and/or attachment means may also be used, including but not limited to snap fit, friction fit, pins, rivets, etc. In some embodiments, once the housing 207 is assembled, such assembly may be considered and/or made permanent using any known suitable means, such as but not limited to adhesives, welding, etc.

Figure 5:
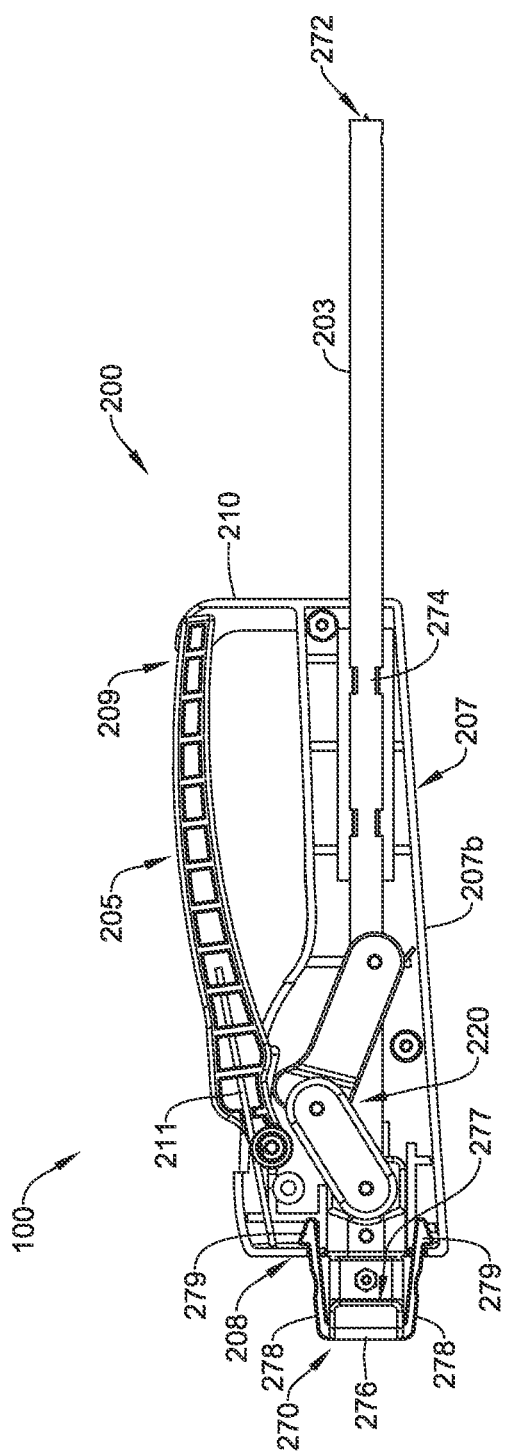
FIG. 5 illustrates aspects of the medical device of FIG. 4 with the lever in an initial or intermediate position.

The medical device 100 may include the bone punch and anchor member delivery system 270 described herein. The bone punch and anchor member delivery system 270 may be disposed within and/or extend through the sheath 203. The head 276 of the bone punch and anchor member delivery system 270 may be releasably engaged with the housing 207 in a first position, as shown in FIGS. 4-5. The piercing tip 272 may be positioned proximate a distal end of the sheath 203 in the first position. In some embodiments, the piercing tip 272 may be disposed within the distal end of the sheath 203 in the first position. In some embodiments, a portion of the piercing tip 272 may extend distally of the distal end of the sheath 203 in the first position to aid in positioning the medical device 100 at a treatment site (e.g., to engage a surface of the bone). In some embodiments, less than 50% of the piercing tip 272 extends distally of the distal end of the sheath 203 in the first position. In some embodiments, less than 40% of the piercing tip 272 extends distally of the distal end of the sheath 203 in the first position. In some embodiments, less than 30% of the piercing tip 272 extends distally of the distal end of the sheath 203 in the first position. In some embodiments, less than 20% of the piercing tip 272 extends distally of the distal end of the sheath 203 in the first position. In some embodiments, less than 10% of the piercing tip 272 extends distally of the distal end of the sheath 203 in the first position. In some embodiments, less than 5% of the piercing tip 272 extends distally of the distal end of the sheath 203 in the first position.

FIG. 5 illustrates the medical device 100 with the first housing portion 207a of the handle assembly 200 removed and the second housing portion 207b visible. The housing 207 may include a leg 210 extending laterally from a distal portion thereof. In some embodiments, the leg 210 may be disposed at and/or extend laterally from the distal end of the housing 207. The lever 205 may be rotatably and/or pivotably coupled to the housing 207 about an axis of rotation. The handle assembly 200 may include a spring 211 biasing the lever 205 toward an initial position, such as an intermediate position. In at least some embodiments, the spring 211 may include a coiled portion disposed about and/or coaxial with the axis of rotation of the lever 205.

In FIG. 5, the lever 205 is shown disposed in the initial or intermediate position. In at least some embodiments, from the initial or intermediate position, the lever 205 may be configured to rotate a distal end 209 of the lever 205 toward or away from the housing 207. In the initial or intermediate position, the distal end 209 of the lever 205 may be substantially aligned with and/or disposed within a free end of the leg 210. In the initial or intermediate position, the lever 205 may extend distally toward a distal end of the sheath 203 and/or the handle assembly 200 at a first angle relative to a longitudinal axis of the sheath 203. For example, the first angle may be less than about 15 degrees, less than about 10 degrees, less than about 5 degrees, about 0 degrees, or another small, oblique angle. In some embodiments, in the initial or intermediate position, the lever 205 may extend toward the distal end of the sheath 203 generally parallel to a longitudinal axis of the sheath 203.

In FIG. 5, the bone punch and anchor member delivery system 270 is shown disposed in the first position. The elongate shaft 274 of the bone punch and anchor member delivery system 270 is slidably disposed within the sheath 203 of the handle assembly 200 when the lever 205 is in the initial or intermediate position. The head 276 of the bone punch and anchor member delivery system 270 may be releasably engaged with the housing 207 of the handle assembly 200 in the first position and/or when the lever 205 is in the initial or intermediate position. For example, the plurality of connecting members 278 and the outwardly extending protrusion(s) 279 thereof may engage a wall of the housing 207 defining a proximal surface 208 of the housing 207. In some embodiments, the proximal surface 208 may be a proximally facing surface of the housing 207 at and/or proximate a proximal end of the housing 207. In some embodiments, the proximal surface 208 may be a proximalmost surface of the housing 207.

In the first position, the outwardly extending protrusion(s) 279 may extend laterally outward from the head 276 and/or the longitudinal axis of the bone punch and anchor member delivery system 270 and/or the elongate shaft 274 beyond a perimeter of an opening in the wall of the housing 207 within which the head 276 is disposed. The outwardly extending protrusion(s) 279 may prevent the head 276 and/or the bone punch and anchor member delivery system 270 from being removed from the housing 207 until the plurality of connecting members 278 are squeezed, urged, actuated, or otherwise moved inward toward the head 276, and/or the longitudinal axis of the bone punch and anchor member delivery system 270 and/or the elongate shaft 274, to disengage the outwardly extending protrusion(s) 279 from the wall of the housing 207 by translating the outwardly extending protrusion(s) 279 inward until the outwardly extending protrusion(s) 279 are disposed within and/or inward of the perimeter of the opening. Doing so will permit the plurality of connecting members 278 and the outwardly extending protrusion(s) 279 to pass through the opening in the wall of the housing 207. In the first position, the one or more lateral projections of the head 276 and/or the distal surface 277 of the head 276 may be spaced apart proximally from the proximal surface 208 of the wall of the housing 207.

Figure 6:
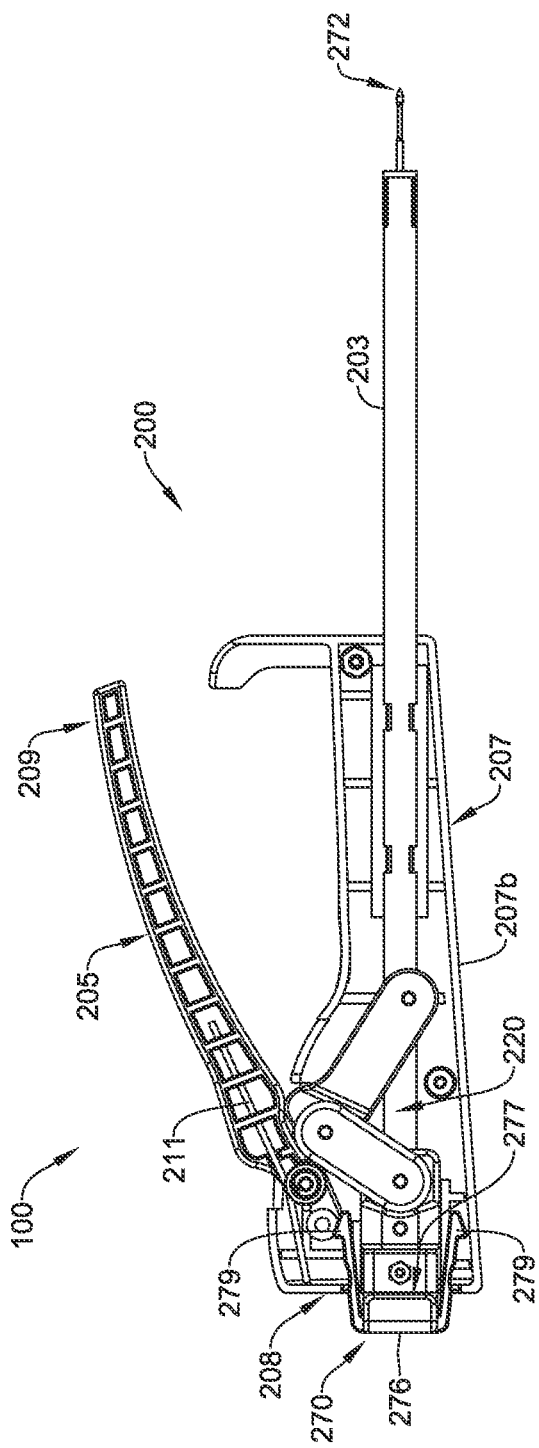
FIG. 6 illustrates aspects of the medical device of FIG. 4 with the lever in an extended position.

In some embodiments, the handle assembly 200 may include a linkage 220 disposed within the housing 207. The linkage 220 will be described in more detail with respect to FIGS. 7-10. As may be seen in FIG. 5, the head 276 of the bone punch and anchor member delivery system 270 may engage the linkage 220 in the first position. The linkage 220 may be pivotably engaged with and/or coupled to the housing 207. The linkage 220 may include a plurality of elements that are movable and/or pivotable relative to each other. Translation of the bone punch and anchor member delivery system 270 distally within the sheath 203, and/or translation of the head 276 of the bone punch and anchor member delivery system 270 distally relative to the housing 207, from the first position to a second position distal of the first position may cause the linkage 220 to rotate the distal end 209 of the lever 205 away from the housing 207 and/or away from the longitudinal axis of the bone punch and anchor member delivery system 270 and/or the elongate shaft 274 to an extended position, as shown in FIG. 6. In the extended position, the lever 205 may extend toward a distal end of the sheath 203 and/or the handle assembly 200 at a second angle relative to the longitudinal axis of the sheath 203. In some embodiments, the second angle may be an oblique angle. The second angle may be greater than the first angle.

As shown in FIG. 6, the distal surface 277 of the head 276 of the bone punch and anchor member delivery system 270 may engage and/or abut the proximal surface 208 of the housing 207 in the second position. In the second position, the outwardly extending protrusion(s) 279 may be spaced apart distally from the wall of the housing 207 defining the proximal surface 208. However, the outwardly extending protrusion(s) 279 may still extend laterally outward from the head 276 and/or the longitudinal axis of the bone punch and anchor member delivery system 270 and/or the elongate shaft 274 beyond the perimeter of the opening in the wall of the housing 207 within which the head 276 is disposed, thus preventing inadvertent removal of the bone punch and anchor member delivery system 270 from the handle assembly 200.

In the second position, the piercing tip 272 may be extended from the distal end of the sheath 203 as the elongate shaft 274 is translated distally within the sheath 203. The distal end of the sheath 203 may be configured to be disposed adjacent a surface of the bone. As the bone punch and anchor member delivery system 270 is translated distally to the second position, the piercing tip 272 may be driven into the bone to form one or more holes in the bone. There may be a direct or indirect correlation between a rotational position of the lever 205 relative to the housing 207 and a depth of the piercing tip 272 within the bone. As the lever 205 rotates farther away from the housing 207 and/or as an angle between the lever 205 and the longitudinal axis of the sheath 203 and/or the bone punch and anchor member delivery system 270 increases, the piercing tip 272 may be extended farther distally from the distal end of the sheath 203 and/or may be driven farther into the bone. A user of the medical device and/or the handle assembly 200 may be able to use the rotational position of the lever 205 relative to the housing 207 and/or the longitudinal axis of the sheath 203 and/or the bone punch and anchor member delivery system 270 to indicate the depth of the piercing tip 272 within the bone, thereby providing a visual cue to the user about the status of the procedure.

Thereafter, rotation of the lever 205 from the extended position (e.g., FIG. 6) toward the initial or intermediate position (e.g., FIG. 5) may generate proximal force on the bone punch and anchor member delivery system 270 sufficient to overcome cortical elasticity of the bone (which is "squeezing" or "pinching" the piercing tip 272) to extract the piercing tip 272 from the bone. Accordingly, rotation of the lever 205 from the extended position (e.g., FIG. 6) toward the initial or intermediate position (e.g., FIG. 5) may generate proximal translation of the bone punch and anchor member delivery system 270 to thereby extract the piercing tip 272 from the bone, leaving the one or more holes formed in the bone. The linkage 220 may provide a mechanical advantage in generating the force necessary to extract the piercing tip 272 from the bone, thereby reducing the force that the user needs to exert on the lever 205. Rotating the lever 205 from the extended position to the initial or intermediate position may translate the bone punch and anchor member delivery system 270 from the second position back to the first position. Thereafter, the bone punch and anchor member delivery system 270 may be removed from the handle assembly 200 if desired, or the medical device 100 may be removed from the treatment site.

Figure 7:
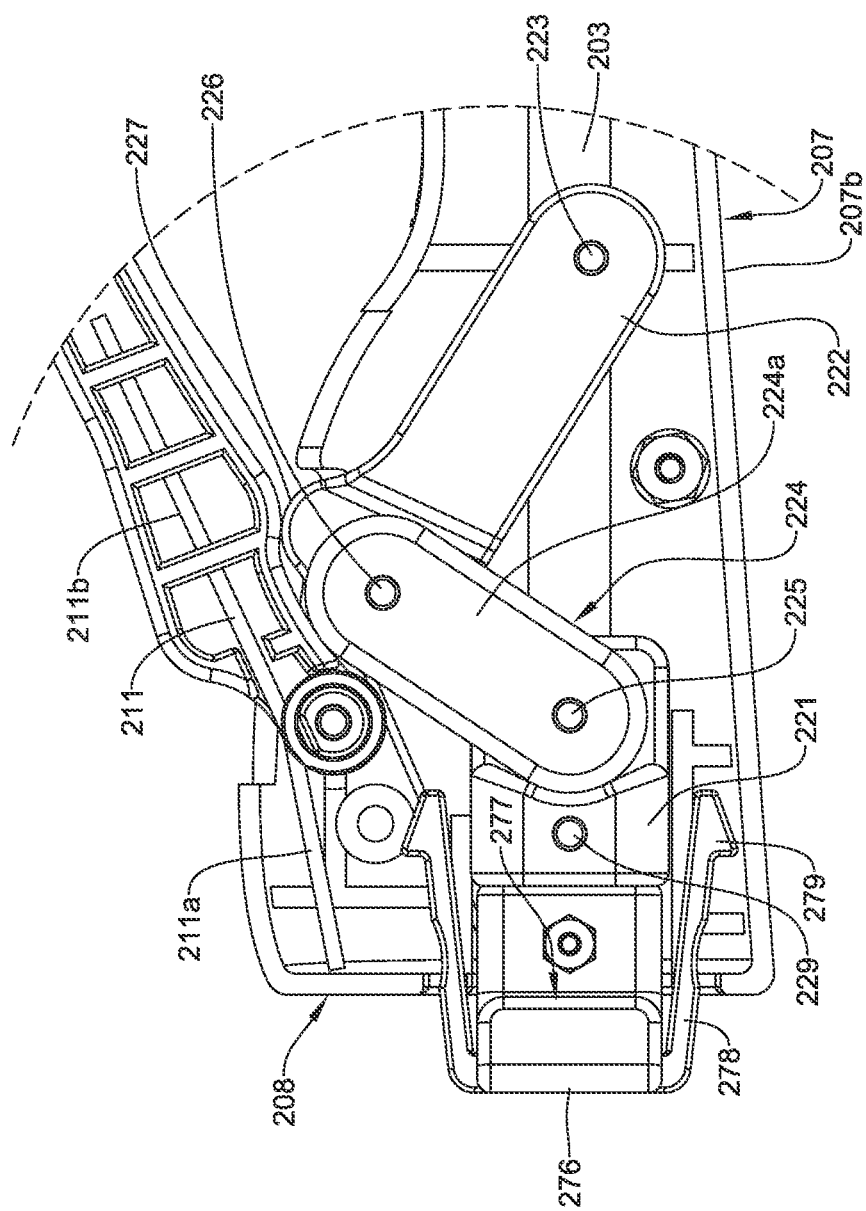
FIG. 7 is a detailed view illustrating aspects of the medical device of FIG. 4 with the lever in the extended position of FIG. 6.

FIG. 7 is a detailed view of a portion of the medical device of FIG. 6, wherein the bone punch and anchor member delivery system 270 is disposed in the second position and the lever 205 is disposed in the extended position. The linkage 220 may include an ejector block 221 slidably disposed within the housing 207. The ejector block 221 may include one or more pins 229 configured to engage the housing 207 and/or configured to slide longitudinally and/or axially within a channel formed in the housing 207. In some embodiments, the ejector block 221 may be configured to slide longitudinally and/or axially within a channel formed in the housing 207. In some embodiments, the ejector block 221 may be configured to slide parallel to the longitudinal axis of the sheath 203 and/or the longitudinal axis of the bone punch and anchor member delivery system 270 and/or the elongate shaft 274. In some embodiments, the sheath 203 may extend through and/or may pass through the ejector block 221. As such, the ejector block 221 may be slidably disposed about the sheath 203. Since the elongate shaft 274 may be slidably disposed within the sheath 203, the elongate shaft 274 may also extend through the ejector block 221. The head 276 of the bone punch and anchor member delivery system 270 may be configured to engage the ejector block 221 in the first position. During distal translation of the bone punch and anchor member delivery system 270 from the first position to the second position, the head 276 of the bone punch and anchor member delivery system 270 may push, urge, or otherwise translate the ejector block 221 distally within the housing 207, thereby actuating the linkage 220 and causing the linkage 220 to rotate the distal end 209 of the lever 205 away from the housing 207 to the extended position.

In at least some embodiments, the linkage 220 may further include a distal link 222 pivotably engaged with the housing 207 at a distal pivot point 223, and a middle link 224 pivotably engaged with the ejector block 221 at a proximal pivot point 225. In some embodiments, the middle link 224 may include a first middle link 224a and a second middle link 224b (not shown). In some embodiments, a proximal portion of the distal link 222 may be disposed between the first middle link 224a and the second middle link 224b. In some embodiments, a distal portion of the distal link 222 may comprise a pair of opposing legs extending on opposite sides of the sheath 203. One leg of the pair of opposing legs may be configured to engage the first housing portion 207a, and one leg (e.g., the opposite leg) of the pair of opposing legs may be configured to engage the second housing portion 207b.

The distal link 222 may be pivotably engaged with the middle link 224 at an intermediate pivot point 226 between the distal pivot point 223 and the proximal pivot point 225. The distal pivot point 223 may be axially and/or longitudinally fixed relative to the housing 207. As such, when the head 276 of the bone punch and anchor member delivery system 270 is translated distally to slide the ejector block 221 distally within the housing 207, a proximal end of the distal link 222 and a distal end of the middle link 224 may be translated laterally relative to the longitudinal axis of the sheath 203, the bone punch and anchor member delivery system 270, and/or the elongate shaft 274 by pivoting relative to each other at the intermediate pivot point 226 as a proximal end of the middle link 224 is translated distally and/or longitudinally toward a distal end of the distal link 222 and/or the distal pivot point 223. In some embodiments, the proximal pivot point 225, the intermediate pivot point 226, and/or the distal pivot point 223 may include and/or be defined by one or more pins, shafts, or other elements. Some examples of suitable but non-limiting materials for the ejector block 221, the distal link 222, the middle link 224, and/or elements or components thereof are described below.

The distal link 222 may include a cam surface 227 configured to engage a corresponding surface of the lever 205, wherein the corresponding surface of the lever 205 faces toward the housing 207, the distal link 222, and/or the longitudinal axis of the sheath 203, the bone punch and anchor member delivery system 270, and/or the elongate shaft 274. In some embodiments, the cam surface 227 may be a curved surface. In some embodiments, the cam surface 227 may be a convex surface. In some embodiments, the corresponding surface of the lever 205 may be a curved surface. In some embodiments, the corresponding surface of the lever 205 may be a convex surface. In some embodiments, the corresponding surface of the lever 205 may be a concave surface. In some embodiments, the corresponding surface of the lever 205 may be a complex and/or an irregular surface having both concave and convex portions. Other configurations are also contemplated.

As discussed above, the handle assembly 200 may include a spring 211 disposed within the housing 207. The spring 211 may include a first arm portion 211a extending proximally from the coiled portion and configured to engage the housing 207. In at least some embodiments, the first arm portion 211a may be configured to engage the first housing portion 207a (not shown). The spring 211 may include a second arm portion 211b extending distally from the coiled portion and configured to engage the lever 205. For example, the lever 205 may include a slot formed therein configured to receive the second arm portion 211b. In another example, the lever 205 may include one or more apertures 206 configured to receive the second arm portion 211b, as seen in FIG. 8.

Figure 8:
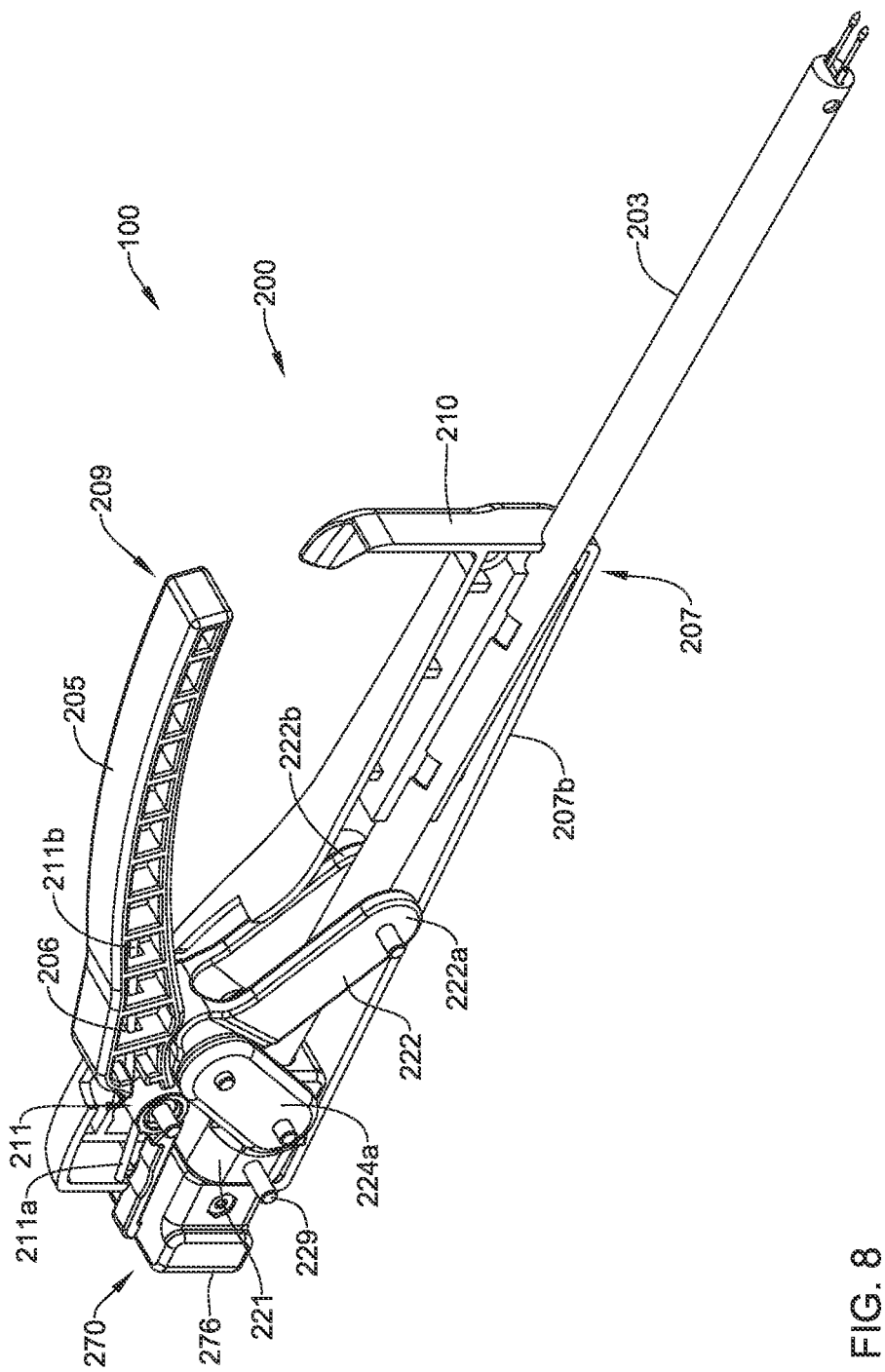
FIGS. 8-10 are perspective views illustrating aspects of the medical device of FIG. 4 with the lever in the extended position of FIG. 6.
Figure 9:
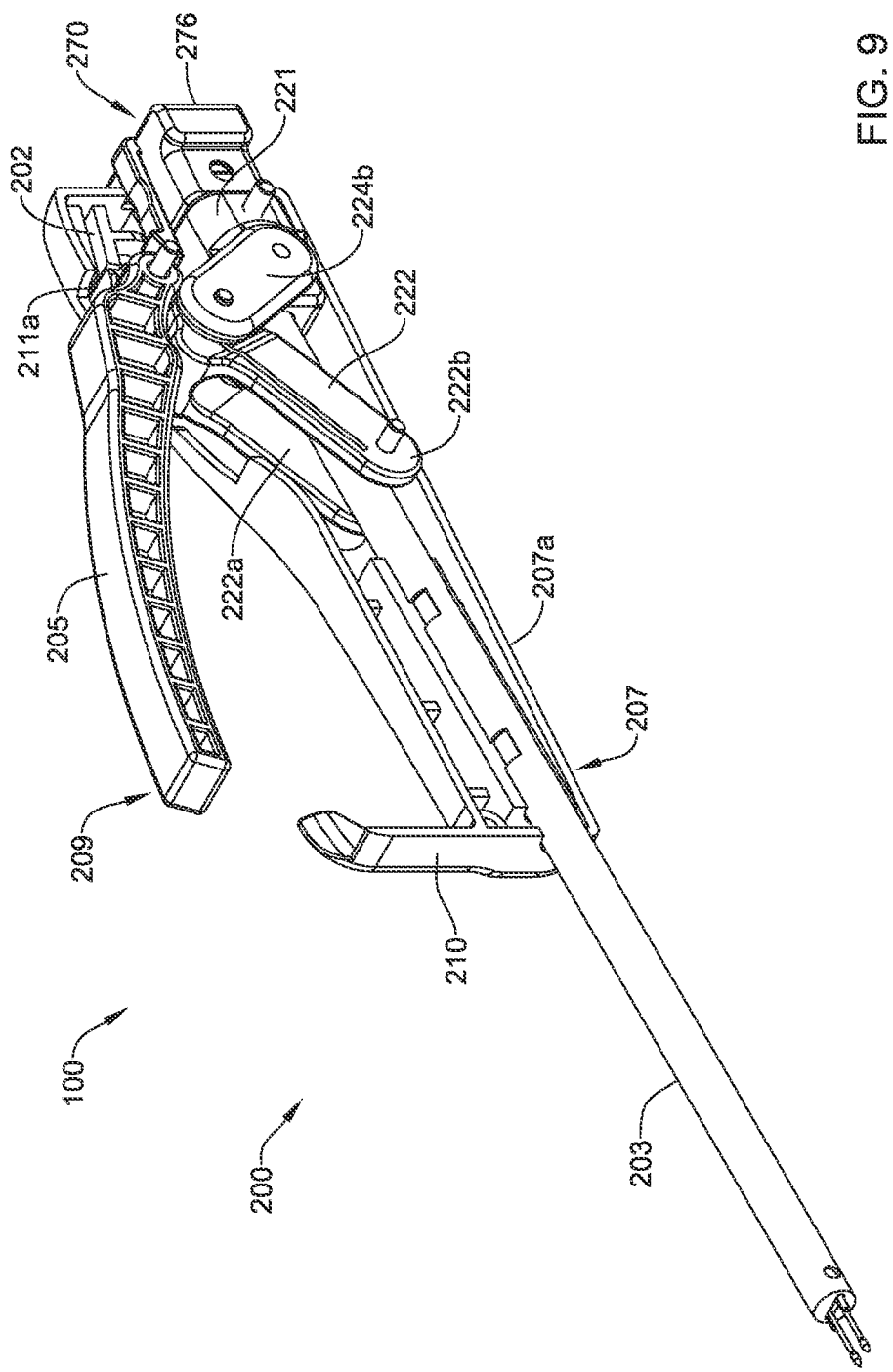
Figure 10:
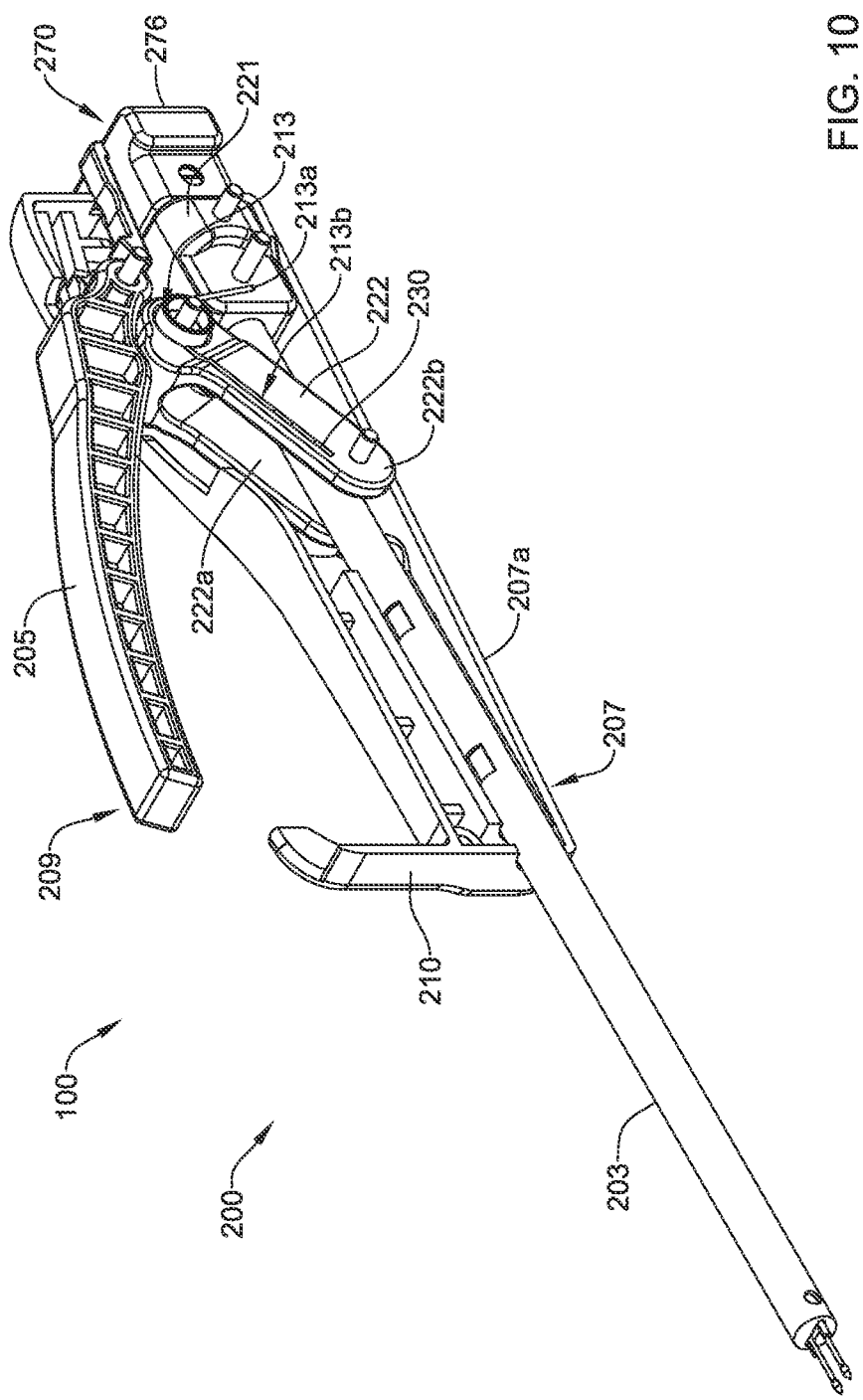

FIGS. 8-10 are perspective views of the medical device 100 and the handle assembly 200 described herein. FIGS. 8-10 are shown from different angles and with different elements of the handle assembly 200 hidden from view show additional features and/or to facilitate understanding of the various interactions between components. For example, in some embodiments, the pair of opposing legs of the distal link 222 may include a first leg 222a and a second leg 222b.

In some embodiments, the first housing portion 207a may include a slot 202 configured to receive the first arm portion 211a of the spring 211, as seen in FIG. 9. Other configurations for securing the first arm portion 211a relative to the first housing portion 207a, and/or preventing relative movement therebetween, are also contemplated. As discussed above, the middle link 224 may include a first middle link 224a (not shown) and a second middle link 224b, shown in FIG. 9. The first middle link 224a and the second middle link 224b may be similar in form, size, and/or shape.

In some embodiments, the handle assembly 200 may include a second spring 213, shown in FIG. 10, may include a coiled portion, a first arm portion 213a extending proximally from the coiled portion, and a second arm portion 213b extending distally from the coiled portion. In some embodiments, the second middle link 224b (not shown) may include a slot formed therein facing and/or opening inwardly and/or toward the proximal portion of the distal link 222. The slot formed in the second middle link 224b may be configured to receive the first arm portion 213a of the second spring 213. The distal link 222 may include a slot 230 formed in the second leg 222b of the pair of opposing legs of the distal link 222, wherein the slot 230 faces and/or opens outwardly and/or toward the second middle link 224b. The slot 230 may be configured to receive the second arm portion 213b of the second spring 213. In some embodiments, at least a portion of the coiled portion of the second spring 213 may be received and/or recessed in the proximal portion of the distal link 222.

Figure 11:
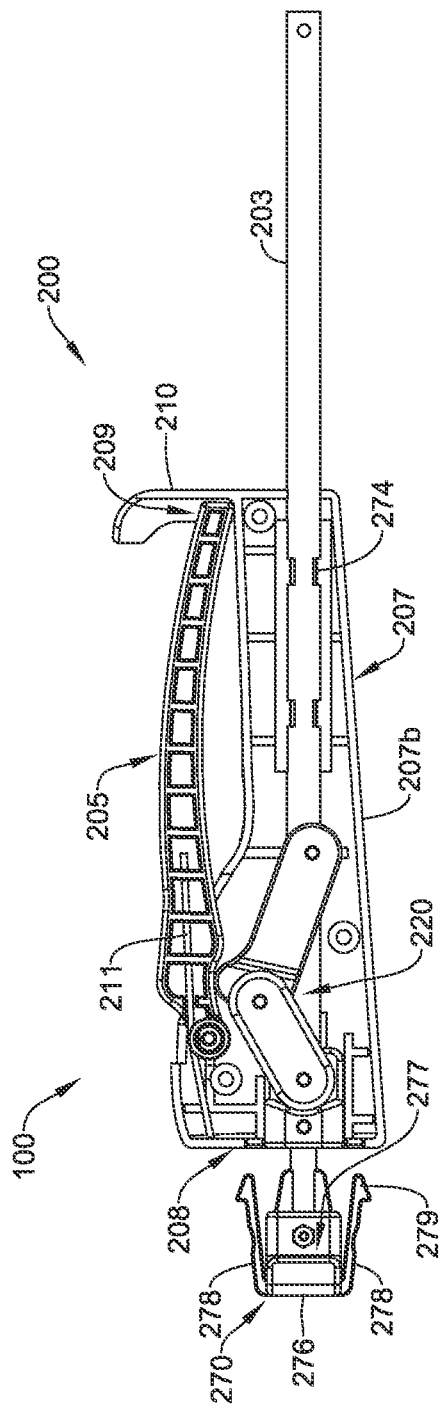
FIG. 11 illustrates aspects of the medical device of FIG. 4 with the lever in a disengagement position.

It will be easily understood that rotation of the lever 205 toward the housing 207 and/or the longitudinal axis of the sheath 203, the bone punch and anchor member delivery system 270, and/or the elongate shaft 274 (e.g., toward the initial or intermediate position) when the bone punch and anchor member delivery system 270 is in the second position may actuate the linkage 220 to translate the head 276 of the bone punch and anchor member delivery system 270 proximally to retract the piercing tip 272 into the sheath 203 and/or to extract the piercing tip 272 from the bone of the patient. The corresponding surface of the lever 205 may exert a force upon the cam surface 227 of the distal link 222, thereby urging and/or translating the proximal portion of the distal link 222 laterally toward the longitudinal axis of the sheath 203, the bone punch and anchor member delivery system 270, and/or the elongate shaft 274, thereby resulting in corresponding movement of the middle link 224 and proximal translation of the ejector block 221 within the housing 207 until the outwardly extending protrusion(s) 279 re-engage the wall of the housing 207. When the outwardly extending protrusion(s) 279 are engaged with the wall of the housing 207, the lever 205 is in the initial or intermediate position and is prevented from rotating inward past the initial or intermediate position and/or closer to the housing 207 than the initial or intermediate position until the outwardly extending protrusion(s) 279 are disengaged from the wall of the housing 207 by squeezing, urging, actuating, or otherwise moving the plurality of connecting members 278 inward toward the head 276, and/or the longitudinal axis of the bone punch and anchor member delivery system 270 and/or the elongate shaft 274. Once the outwardly extending protrusion(s) 279 are disengaged from the wall of the housing 207, the lever 205 may be rotated toward the housing 207 and/or the longitudinal axis of the sheath 203, the bone punch and anchor member delivery system 270, and/or the elongate shaft 274 toward a disengagement position, shown in FIG. 11, to aid in ejecting the bone punch and anchor member delivery system 270 from the handle assembly 200.

The spring 211 may be biased toward the initial or intermediate position of the lever 205. As such, if the lever 205 is rotated away from the initial or intermediate position, the spring 211 may be stressed and may exert a force on the lever 205 to return the lever 205 to the initial or intermediate position. The initial or intermediate position of the lever 205 may be considered a "home" position for the spring 211. Similarly, the second spring 213 may be biased toward the disengagement position of the lever 205. As such, if the lever 205 is rotated away from the disengagement position, the second spring 213 may be stressed and may exert a force on the linkage 220 to return the lever 205 to the disengagement position. The disengagement position of the lever 205, and the corresponding positioning of the linkage 220, may be considered a "home" position for the second spring 213. The spring 211 may be configured to exert a greater force on the lever 205 than the second spring 213 is configured to exert on the linkage 220. Effectively, the spring 211 is "stronger" than the second spring 213 and the force exerted by the spring 211 may override the force exerted by the second spring 213. This relationship may also require less force to be applied to the lever 205 to rotate the lever 205 from the extended position toward the initial or intermediate position and/or the disengagement position than to rotate the lever 205 from the initial or intermediate position to the extended position. In other instances, the handle assembly 200 may be configured such that the spring 213 may be configured to exert a greater force on the lever than the spring 211. If all external forces are removed from the handle assembly 200, the lever 205 will be biased toward and/or will return to the initial or intermediate position. If the bone punch and anchor member delivery system 270 is not present within the handle assembly 200, the lever 205 will be biased toward and/or will return to the initial or intermediate position.

Figure 12:
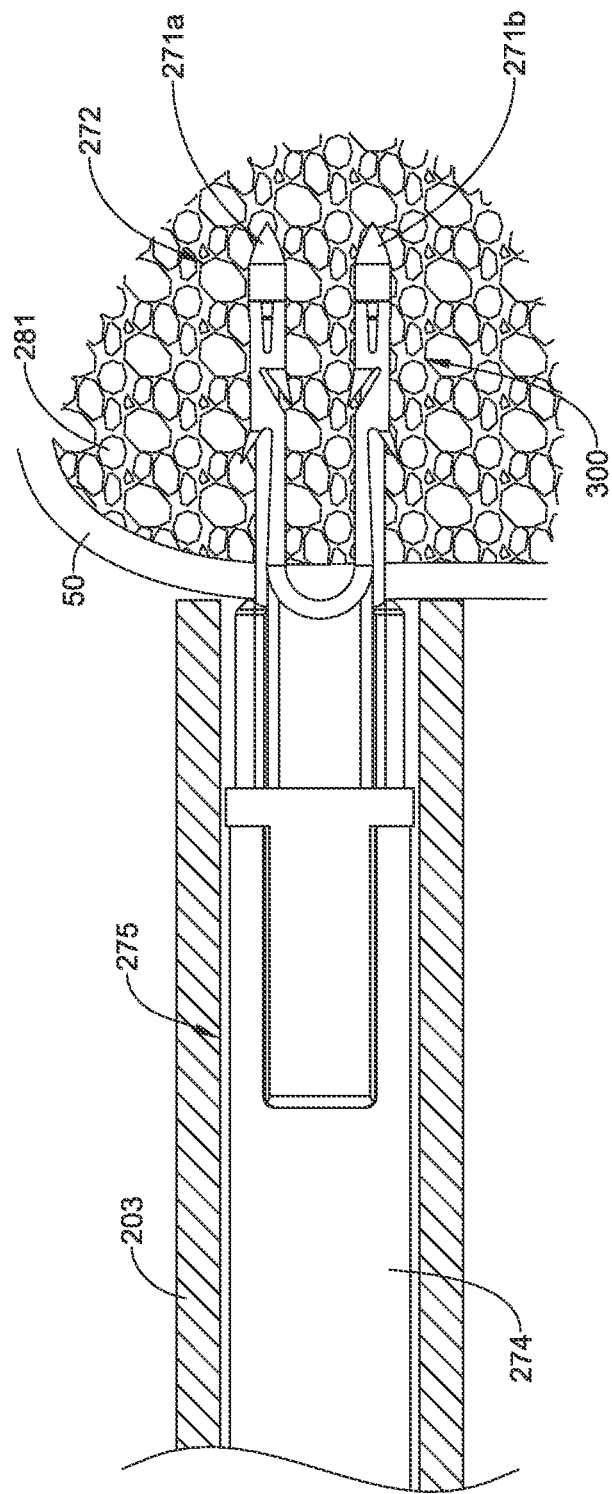
FIG. 12 is a partial cross-sectional view depicting the medical device of FIG. 4 and the bone punch and anchor member delivery system of FIG. 3 disposed at an implant site after the bone punch has been driven into bone at the implant site.
Figure 13:
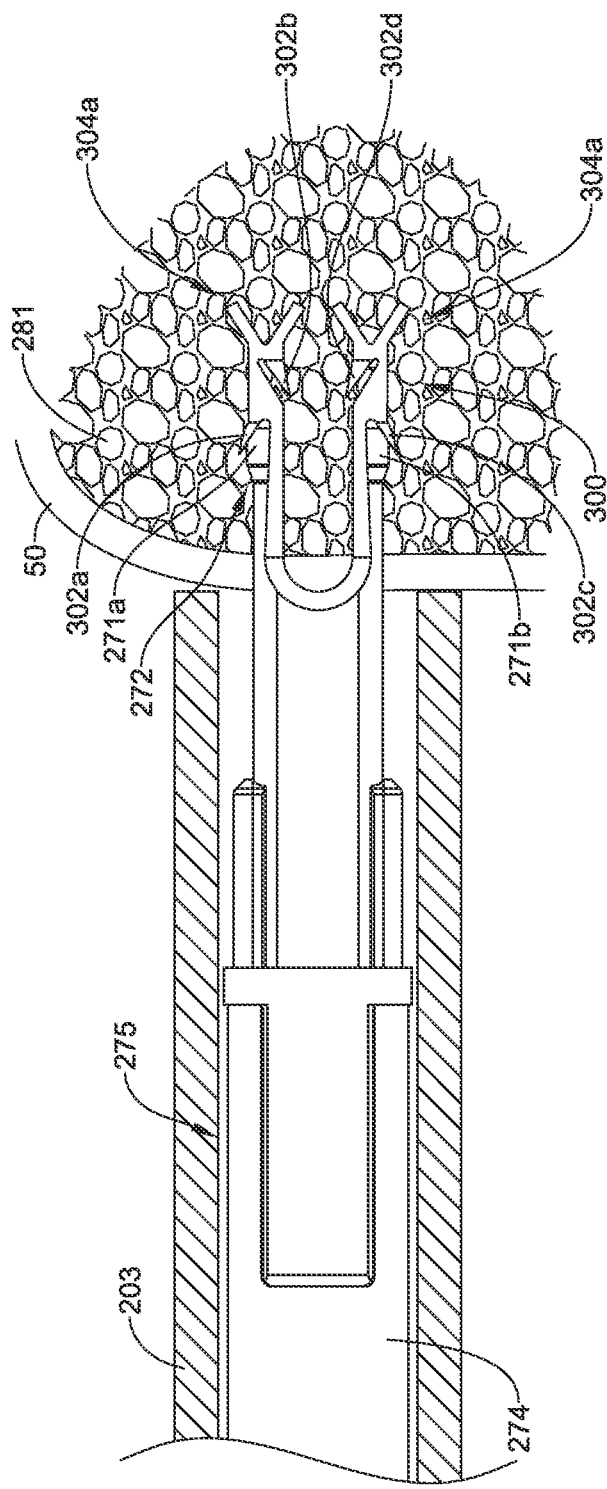
FIG. 13 is a partial cross-sectional view depicting the medical device of FIG. 4 and the bone punch and anchor member delivery system of FIG. 3 disposed at an implant site after the bone punch has been driven into and partially removed from bone at the implant site.
Figure 14:
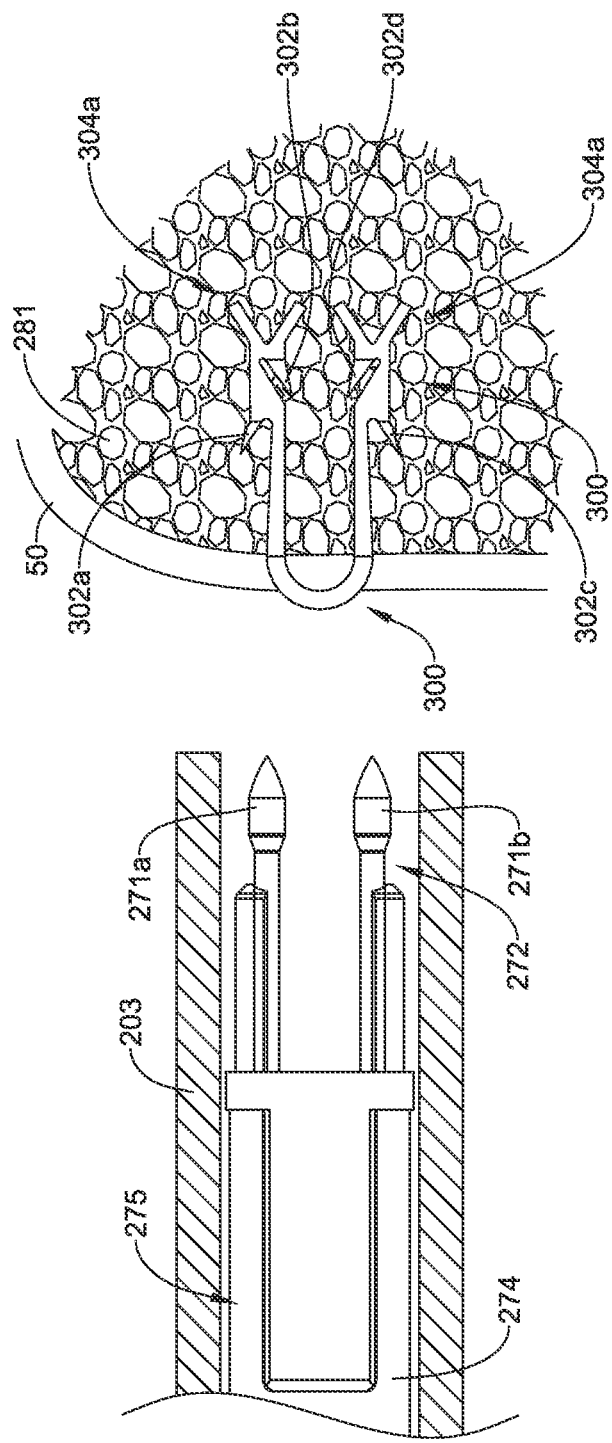
FIG. 14 is a partial cross-sectional view depicting the medical device of FIG. 4 and the bone punch and anchor member delivery system of FIG. 3 disposed at an implant site after the bone punch has been driven into and removed from bone at the implant site.

FIGS. 12-14 illustrate a method for driving the piercing tip 272 into a bone and delivering an anchor member 300 to affix a sheet-like implant 50 of other repair scaffold to a bone. In use, the distal end of the sheath 203 may be configured to be positioned adjacent and/or against the surface of a sheet-like implant 50 placed against a surface of a bone of the patient. As discussed herein, the medical device 100 may be configured to form one or more holes within the bone for insertion of a bone anchor therein. In some embodiments, the distal end of the sheath 203 may be positioned directly against the surface of the bone. In some embodiments, the distal end of the sheath 203 may be positioned against a sheet-like implant 50 that is positioned directly against the surface of the bone, as shown in FIG. 12 for example, so that the one or more holes may also be formed in the sheet-like implant 50. As such, the presence of the sheet-like implant 50 as positioned in FIG. 12 may be considered optional.

After positioning the piercing tip 272 against the surface of the bone 281, the user may apply distal force to the head 276 of the bone punch and anchor member delivery system 270, such as with a mallet or other tool, to drive the piercing tip 272 into the bone 281, as shown in FIG. 12. An anchor member 300, such as a staple, anchor, or other securement member may be loaded onto the piercing tip 272 prior to driving the piercing tip 272 into the bone 281 so that as the piercing tip 272 is driven into the bone 281, at least a portion of the anchor member 300 is concurrently or substantially simultaneously driven into the bone 281 with the piercing tip 272. The piercing tip 272 creates a bore hole (or a plurality of bore holes) into the bone 281 large enough for the distal end region(s) 304a, 304b of the anchor member 300 to be inserted into the bore hole(s) for affixment to the bone 281.

It is noted that the lever 205 may rotate outward, as described above, as the elongate shaft 274 is moved distally relative to the sheath 203 and housing 207 to drive the piercing tip 272 into the bone 281. Next, as the lever 205 is rotated toward the housing 207 to move the elongate shaft 274 proximally relative to the sheath 203 and housing 207, and thus extract the piercing tip 272 from the bone 281, the anchor member 300 remains positioned within the one or more bore holes to affix the sheet-like implant 50 to the bone 281, as shown in FIG. 13. The anchor member 300 may include retention features, such as but not limited to, barbs 302a, 302b, 302c, 302d that are configured to hold the anchor member 300 within the bone 281 as the piercing tip 272 is extracted. The barbs 302 may extend at an acute angle to a longitudinal axis of the anchor member 300 with a tip of the barb 302 extending in a proximal direction. This configuration may facilitate distal movement of the anchor member 300 into the bone 281 while limiting or precluding proximal retraction of the anchor member 300 with the piercing tip 272. As will be described in further detail herein, the distal end regions 304a, 304b may be configured to radially deform (e.g., undergo plastic deformation) as the piercing tip 272 is proximally retracted from the anchor member 300.

Rotation of the lever 205 to its initial or intermediate position (as shown in FIG. 5) may fully disengage the piercing tip 272 from the bone 281, as shown in FIG. 14. In some embodiments, the connecting members 278 of the bone punch and anchor member delivery system 270 may be depressed to remove the bone punch and anchor member delivery system 270 from the handle assembly 200 while leaving the handle assembly 200 in position near the bone 281. In other embodiments, the bone punch and anchor member delivery system 270 and the handle assembly 200 may be removed from the treatment site while the bone punch and anchor member delivery system 270 is still engaged with the handle assembly 200.

Figure 15:
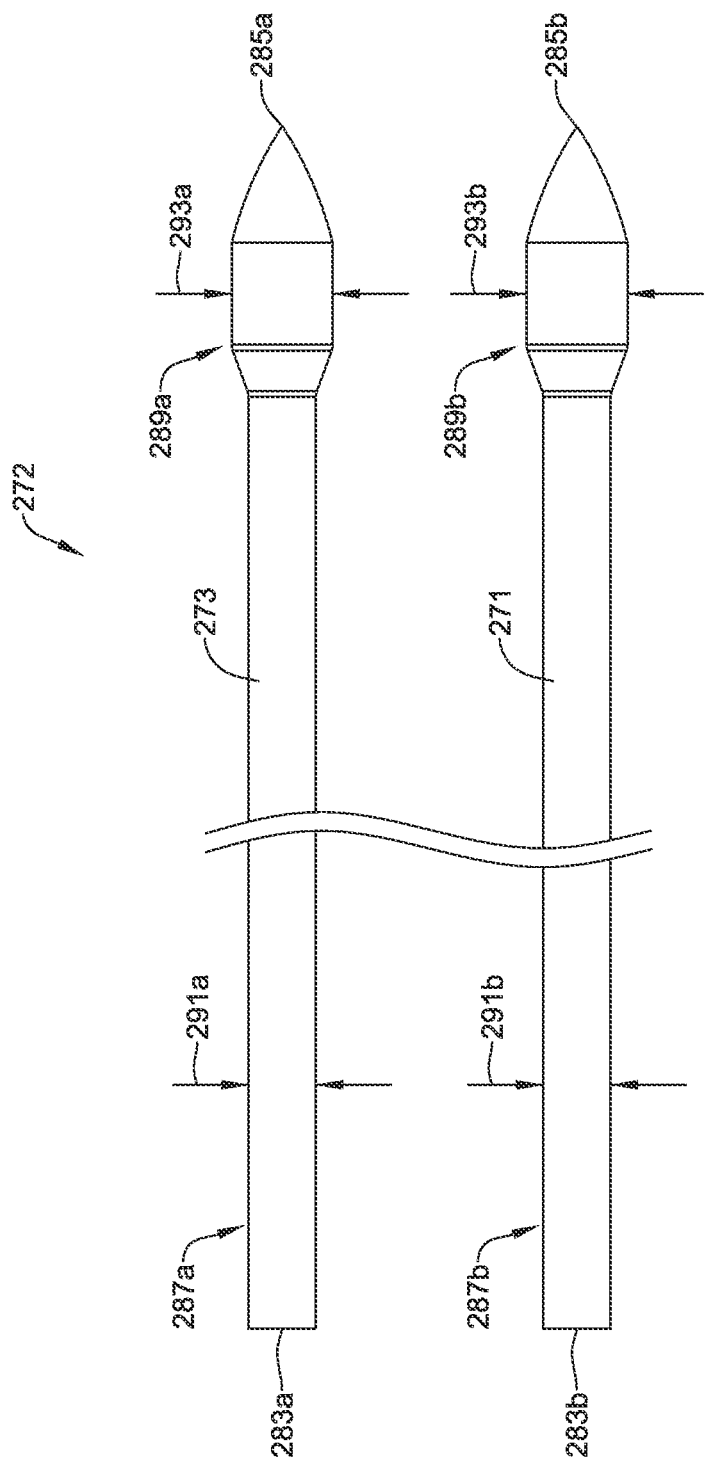
FIG. 15 is a cross-sectional view of the piercing tip.

FIG. 15 illustrates a cross-sectional view of the piercing tip 272. As described herein, the piercing tip 272 may include a first piercing element 271a and a second piercing element 271b extending parallel to the first piercing element 271a. Each piercing element 271 may extend from a proximal end 283a, 283b to a distal end 285a, 285b. A proximal end region 287a, 287b of the piercing elements 271a, 271b (e.g., elongate shaft) extends distally from the proximal end 283a, 283b and may have a generally uniform outer diameter 291a, 291b. The piercing elements 271a, 271b may each have a distal end region 289a, 289b. At least some of the length of the distal end regions 289a, 289b may include an enlarged region having an outer diameter 293a, 293b that is greater than the outer diameter 291a, 291b of the proximal end region 287a, 287b located proximal of the enlarged distal end region 289a, 289b. As described herein the distal ends 285a, 285b include a sharpened or tapered shape extending distally from the enlarged distal end region 289a, 289b and configured to engage and/or penetrate the bone. In some embodiments, a proximal portion of the distal end regions 289a, 289b may be tapered in a proximal direction, such as tapered down to the diameter of the shaft forming the proximal end region 287a, 287b, although this is not required.

Figure 16A:
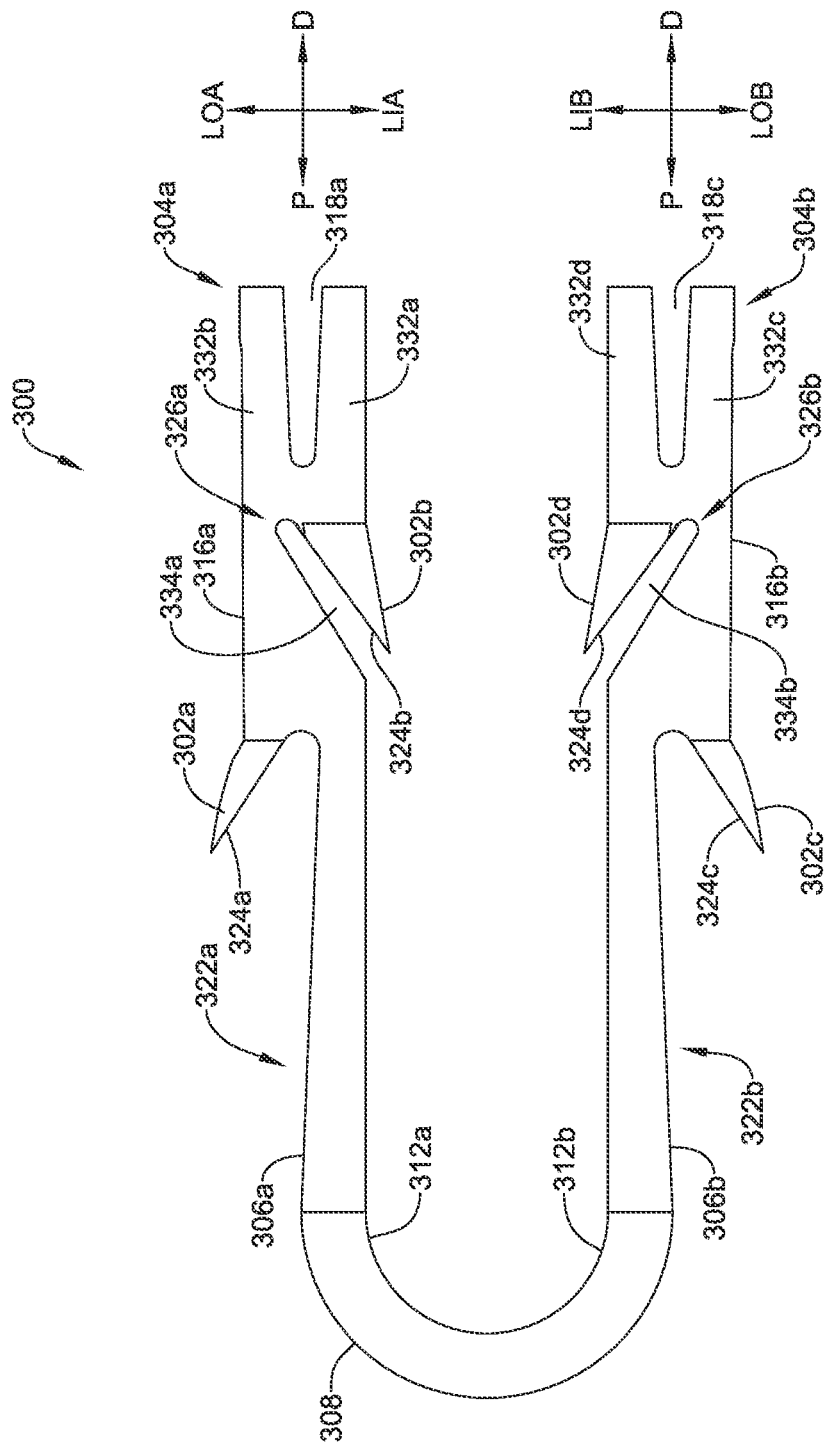
FIG. 16A is a side view of an illustrative anchor member.
Figure 16B:
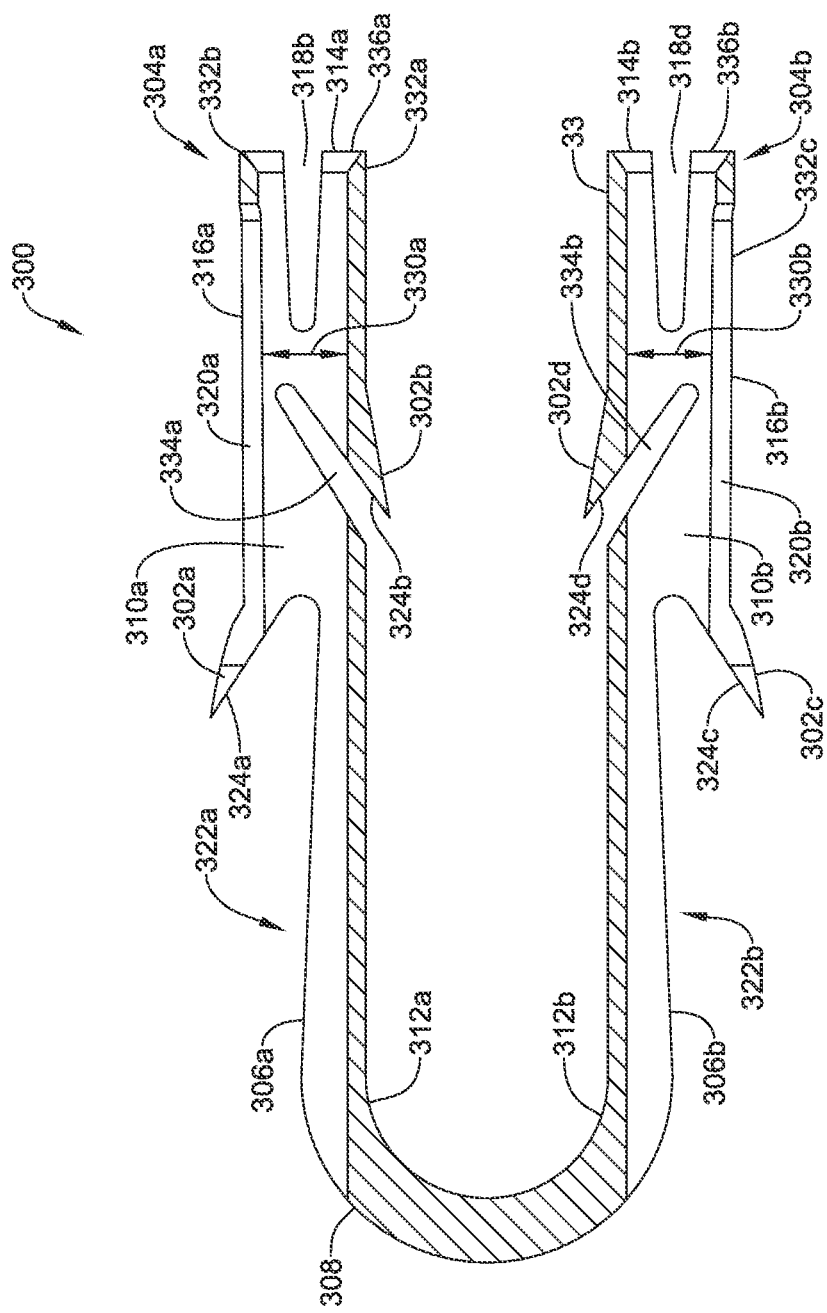
FIG. 16B is a cross-sectional view of the illustrative anchor member of FIG. 16A.

FIG. 16A illustrates a side view of the illustrative anchor member 300 (e.g., staple) and FIG. 16B illustrates a cross-sectional view of the anchor member 300. Although the various parts of the exemplary anchor member 300 are depicted in relative proportion to other parts of the anchor member 300, other configurations in size and orientation of the various parts are also contemplated in other examples. A number of reference directions are illustrated using arrows in FIG. 16A to assist in understanding the details of the anchor member 300. The illustrated directions include: proximal direction P, distal direction D, first laterally outward direction LOA, second laterally outward direction LOB, first laterally inward direction LIA, and second laterally inward direction LIB. In some instances, the anchor member 300 may be a monolithic structure formed of a polymer material, such as polyetheretherketone (PEEK), or a metallic material, such as stainless steel or nitinol. In other instances, the anchor member 300 may include portions formed of a combination of multiple materials.

In some examples, the anchor member 300 comprises a first leg 306a, a second leg 306b, and a bridge portion 308 extending between and connecting the first leg 306a and the second leg 306b. The curved bridge 308 may abut and/or extend between and connect the proximal end 312a of the first leg 306a and the proximal end 312b of the second leg 306b. The first leg 306a may include a first trunk 316a, with the first trunk 316a generally having a greater width than the rest of the first leg 306a (e.g., a non-trunk portion 322a) as depicted in FIGS. 16A and 16B. In some examples, the first trunk 316a may be generally tubular and define a lumen 310a extending therethrough. The length of the first trunk 316a relative to the overall length of the first leg 306a can vary in different examples. For instance, the first trunk 316a can extend for the entire length of the first leg 306a such that the bridge 308 abuts with or is adjacent to the first trunk 316a. When present, the non-trunk portion 322a may have a generally concave shape configured to conform to a convex outer surface of the proximal end region 287a of the first piercing element 271a. For example the non-trunk portion 322a may have a concave surface facing laterally outwardly to face or be juxtaposed with the convex outer surface of the proximal end region 287a of the first piercing element 271a.

Similarly, the second leg 306b may include a second trunk 316b, with the second trunk 316b generally having a greater width than the rest of the second leg 306b (e.g., a non-trunk portion 322b). Additionally, the second trunk 316b may extend for at least a portion of the second leg 306b. In some examples, the second trunk 316b may be generally tubular and define a lumen 310b extending therethrough. The length of the second trunk 316b relative to the overall length of the second leg 306b can vary in different examples. For instance, the second trunk 316b can extend for the entire length of the second leg 306b such that the bridge 308 abuts with or is adjacent to the second trunk 316b. When present, the non-trunk portion 322b may have a generally concave shape configured to conform to a convex outer surface of the proximal end region 287b of the second piercing element 271b. For example the non-trunk portion 322b may have a concave surface facing laterally outwardly to face or be juxtaposed with the convex outer surface of the proximal end region 287b of the second piercing element 271b. In FIGS. 16A and 16B, the first trunk 316a and the second trunk 316b are shown extending distally from a proximal portion of the first leg 306a and the second leg 306b, respectively.

In the example of FIGS. 16A and 16B, the first trunk 316a has a lateral extent, or cross-sectional area, that is larger than a lateral extent of the non-trunk portion 322a of the first leg 306a and the bridge 308. The anchor member 300 may include a first change in lateral stiffness disposed where the distal end of the non-trunk portion 322a of the first leg 306a abuts the first trunk 316a. As depicted, the change in the lateral extent and thus the change in stiffness is abrupt, but can be gradual in alternative examples—such as through a gradual change in lateral extent between the first trunk 316a and the non-trunk portion 322a. In an example where the first trunk 316a extends for the full length of the first leg 306a, the change in stiffness may occur where the first trunk 316a abuts the bridge 308. With reference to the example of FIGS. 16A and 16B, it will be appreciated that the first trunk 316a is mounted eccentrically to the first leg 306a and the second trunk 316b is mounted eccentrically to the second leg 306b. As with the first trunk 316a, the second trunk 316b has a lateral extent, or cross-sectional area that is larger than a lateral extent of the non-trunk portion 322b of the second leg 306b and the bridge 308. The anchor member 300 may include a second change in lateral stiffness where the distal end of the non-trunk portion 322b of the second leg 306b abuts the second trunk 316b. Similarly to the first leg 306a, in some examples, the change in stiffness may be abrupt or gradual. If the second trunk 316b extends for the entire length of the second leg 306b, the change in stiffness may occur at the abutment with the bridge 308. In additional examples where there may be no change in lateral extent between the first and second trunks 316a, 316b and the first and second legs 306a, 306b, respectively, a change in stiffness may be accomplished by the use of different materials for the first and second trunks 316a, 316b and the first and second legs 306a, 306b.

As described above, some examples of the anchor member 300 may include at least a first projection or barb 302a and a second projection or barb 302b on the first trunk 316a longitudinally spaced apart from one another, and a third projection or barb or barb 302c and a fourth projection 302d on the second trunk 316b longitudinally spaced apart from one another. The first and third projections 302a, 302c on the first and second trunks 316a, 316b, respectively, may further include a first proximal surface 324a and a third proximal surface 324c, respectively, each extending away from its respective trunk in a first direction, such as out and away from each opposite trunk 316a, 316b. The first direction may be a direction such that the first and third proximal surfaces 324a, 324c will engage with tissue or bone after the trunk is inserted therein and by natural movement of the tissue or bone. In some examples, a pullout force may be applied to the bridge 308 to further engage the first and third proximal surfaces 324a, 324c with the bone or tissue. The natural movement of the bone or tissue or the pullout force creates a first moment centered on the area of reduced stiffness adjacent each trunk 316a, 316b, tending to rotate each trunk 316a, 316b thereabout. The rotation of each trunk 316a, 316b may further provide a greater holding force of the anchor member 300 in bone or tissue. The second projection 302b and the fourth projection 302d on the first and second trunks 316a, 316b, respectively, may include a second proximal surface 324b and a fourth proximal surface 324d, respectively, extending away from its respective trunk in a second direction, different from the first direction, such as inward, toward the opposite trunk. For example, the second direction may be selected such that the second and fourth proximal surfaces 324b, 324d will engage tissue or bone after each trunk is inserted therein and by natural movement of the tissue or bone. In some examples, a pullout force may be applied to the bridge 308. A slit or area of reduced cross-section in each trunk adjacent the second and fourth projections 302b, 302d provide an area of weakness so that a second moment is applied to the trunk in response to natural movement of the tissue or bone and/or to a pullout force on the bridge 308. This moment causes rotation of the trunk 316a, 316b about the area of weakness and increases the holding force of the anchor member 300.

As illustrated in the example of the anchor member 300 in FIGS. 16A and 16B, the first trunk 316a includes the first projection 302a disposed at a laterally outer side LOA of the first trunk 316a and the second projection 302b disposed at a laterally inner side LIA of the first trunk 316a. The first projection 302a includes the first proximal surface 324a extending away from the first trunk 316a in the first direction. With reference to FIGS. 16A and 16B, it will be appreciated that the first direction has an outward lateral component and a proximal component so that the first proximal surface 324a extends outwardly and proximally away from the first trunk 316a. For example, the first direction may be selected such that the first proximal surface 324a will engage tissue or bone proximate the outer side of the first trunk 316a after being inserted therein so that a first moment is applied to the first trunk 316a in response to natural movement of the tissue or bone and/or to a pullout force on the bridge 308. The moment centers on the arm portion of lesser stiffness adjacent the first projection 302a.

In the example of FIGS. 16A and 16B, the first trunk 316a includes a first localized area of weakness 326a disposed proximate the second projection 302b. The second projection 302b includes the second proximal surface 324b extending away from the first trunk 316a in a second direction. The second direction is selected such that the second proximal surface 324b will engage tissue or bone proximate the inner side of the first trunk 316a when inserted therein so that a second moment is applied to the first trunk 316a in response to natural movement of the tissue or bone and/or a pullout force on the bridge 308. The moment centers around the first localized area of weakness 326a. The second moment has a direction that is generally opposite a direction of the first moment. It will be appreciated that the second direction has an inward lateral component and a proximal component so that the second proximal surface 324b extends inwardly and proximally away from the first trunk 316a. In other examples, the first leg 306a may not include the second projection 302b. In such examples, only a first moment may be applied to the first trunk 316a in response to natural movement of the tissue or bone and/or a pullout force on the bridge 308.

The second trunk 316b includes the third projection 302c disposed at an outer side LOB of the second trunk 316b and the fourth projection 302d disposed at an inner side LIB of the second trunk 316b. In the example of FIGS. 16A and 16B, the third projection 302c includes a third proximal surface 324c extending away from second trunk 316b in a third direction. With reference to FIGS. 16A and 16B, it will be appreciated that the third direction has an outward lateral component and a proximal component so that the third proximal surface 324c extends outwardly and proximally away from the second trunk 316b. The third direction is selected such that the third proximal surface 324c will engage tissue or bone proximate the outer side of the second trunk 316b when inserted therein so that a third moment is applied to the second trunk 316b in response to natural movement of the tissue or bone and/or a pullout force on bridge 308.

In the example of FIGS. 16A and 16B, the second trunk 316b includes a second localized area of weakness 326b disposed proximate the fourth projection 302d. The fourth projection 302d includes a fourth proximal surface 324d extending away from the second trunk 316b in a fourth direction. In the example of FIGS. 16A and 16B, the fourth direction is selected such that the second proximal surface 324b will engage tissue or bone proximate the inner side of the second trunk 316b when inserted therein so that a fourth moment is applied to the second trunk 316b in response to natural movement of the tissue or bone and/or a pullout force on the bridge 308. The fourth moment has a direction that is generally opposite a direction of the third moment. It will be appreciated that the fourth direction has an inward lateral component and a proximal component so that the fourth proximal surface 324d extends inwardly and proximally away from the second trunk 316b. In other examples, the second leg 306b may not include the fourth projection 302d. In such examples, only a first moment may be applied to the second trunk 316b in in response to natural movement of the tissue or bone and/or a pullout force on the bridge 308.

While not explicitly shown, in some embodiments, the anchor member 300 includes proximal projections that extend away from or outward from the bridge 308, while the distal projections extend inward or toward the center of the bridge 308. This creates generally opposing forces in response to tension on the bridge 308 which, in combination with areas of weakness or reduced lateral extent, substantially increases the holding force of the anchor member 300 in bone as the different portions of the trunks tend to rotate in opposite directions and apply force to an opposing wall in the hole in the bone in which the anchor member 300 is positioned. It is however, understood that other configurations of the projections are possible. In some examples, only two projections are included and they extend in different directions to cause different force responses as tension is applied to the bridge 308. Additional examples may include varying numbers of projections which produce one or more moments in each of the first and second legs 306a, 306b.

In some examples, each projection of the anchor member 300 may be divided (e.g., bifurcated) to form a plurality of points for greater retention in tissue or bone. In the example of FIGS. 16A and 16B, the first projection 302a of the first trunk 316a defines a first notch (not explicitly shown) that divides the first projection 302a into a first sub-projection and a second sub-projection. The second projection 302b of the second trunk 316b defines a second notch 328b (see, for example, FIG. 17). The second notch 328b may be similar in form and function to the first notch. In the example of FIGS. 16A and 16B, the second notch 328b divides the second projection 302b into a first sub-projection and a second sub-projection. While not explicitly shown, the third projection 302c of the second trunk 316b may a third notch that divides the third projection 302c into a first sub-projection and a second sub-projection and the fourth projection 302d of the second trunk 316b may define\ a fourth notch that divides the fourth projection 302d into a first sub-projection and a second sub-projection, although this is not required.

With continued reference to FIGS. 16A and 16B, the first trunk 316a defines a first lumen or cavity 310a and the second trunk 316b defines a second lumen or cavity 310b. The first lumen 310a extends into the first trunk 316a and the second lumen 310b extends into the second trunk 316b. The first and second lumens 310a, 310b are sized to cooperate with the piercing tip 272 for holding and inserting the staple into tissue or bone. As described above, the piercing tip 272 includes longitudinally extending piercing elements 271a, 271b that fit within (e.g., extend through) the first and second lumens 310a, 310b to hold the anchor member 300 and push it into position in the tissue or bone as the piercing elements 271a, 271b abuts a portion of its respective trunk. The first lumen 310a and the second lumen 310b may extend through the entire length of the first trunk 316a and the second trunk 316b, respectively, or other portions of the anchor member 300 in some examples. In some embodiments, the first lumen 310a and the second lumen 310b each have a generally circular or oblong cross-sectional shape to cooperate with a similarly shaped cross-section on the piercing elements 271a, 271b. However, the first lumen 310a and the second lumen 310b may have various cross-sectional shapes to cooperate with alternative staple delivery insert designs without deviating from the spirit and scope of the present disclosure. At least a portion of the first lumen 310a may extend laterally outward beyond the lateral outward extent of the bridge 308 and the non-trunk portion 322a. Likewise, at least a portion of the second lumen 310b may extend laterally outward beyond the lateral outward extent of the bridge 308 and the non-trunk portion 322b.

The first lumen 310a may have a first diameter or cross-sectional dimension 330a. The first diameter 330a may be greater than or approximately the same as the outer diameter 291a of the proximal end region 287a of the piercing element 271a such that the proximal end region 287a freely slides within the first lumen 310a. The first diameter 330a may be less than the outer diameter 293a of the enlarged distal end region 289a of the piercing element 271a such that there is a mechanical engagement between the distal end 314a of the first leg 306a and the enlarged distal end region 289a. This may limit undesired distal movement or deployment of the anchor member 300 relative to the piercing tip 272 or undesired proximal retraction of the piercing tip 272 relative to the anchor member 300. Furthermore, the outer diameter 293a of the enlarged distal end region 289a may be substantially similar (i.e., within 10%) to the outer lateral extent (e.g., outer diameter) of the first trunk 316a at its distal end such that the enlarged distal end region 289a may form a bore hole large enough to receive the first trunk 316a therein (prior to radial expansion or plastic deformation of the first and second trunks 316a, 316b). For instance, the outer lateral extent (e.g., outer diameter) of the first trunk 316a may be equal to or less than the outer diameter 293a of the enlarged distal end region 289a, such as between 0-10% less than the diameter 293a of the enlarged distal end region 289a. Similarly, the second lumen 310b may have a second diameter or cross-sectional dimension 330b. The second diameter 330b may be approximately the same as the first diameter 330a and may be greater than or approximately the same as the outer diameter 291b of the proximal end region 287b of the piercing element 271b such that the proximal end region 287b freely slides within the second lumen 310b. The second diameter 330b may be less than the outer diameter 293b of the enlarged distal end region 289b of the piercing element 271b such that there is a mechanical engagement between the distal end 314b of the second leg 306b and the enlarged distal end region 289b. This may limit undesired distal movement or deployment of the anchor member 300 relative to the piercing tip 272 or undesired proximal retraction of the piercing tip 272 relative to the anchor member 300. Furthermore, the outer diameter 293b of the enlarged distal end region 289b may be substantially similar (i.e., within 10%) to the outer lateral extent (e.g., outer diameter) of the second trunk 316b at its distal end such that the enlarged distal end region 289b may form a bore hole large enough to receive the second trunk 316b therein (prior to radial expansion or plastic deformation of the first and second trunks 316a, 316b). For instance, the outer lateral extent (e.g., outer diameter) of the second trunk 316b may be equal to or less than the outer diameter 293b of the enlarged distal end region 289b, such as between 0-10% less than the diameter 293b of the enlarged distal end region 289b.

The anchor member 300 may include features which allow the piercing tip 272 to be proximally retracted through the lumens 310a, 310b to deploy the anchor member 300 within the tissue or bone. The first and second trunks 316a, 316b may radially expand or be deformed to permit the enlarged distal end regions 289a, 289b to be withdrawn proximally through the lumens 310a, 310b. In some instances, the retraction of the enlarged distal end regions 289a, 289b through the lumens 310a, 310b may cause the first and second trunks 316a, 316b to undergo plastic deformation as the first and second trunks 316a, 316b radially expand. For example, the first and second trunks 316a, 316b may each include one or more slots, slits, or channels extending partially or completely through a thickness of the wall of the first and second trunks 316a, 316b and that are configured to facilitate radial expansion of at least some regions of the first and second trunks 316a, 316b.

The first leg 306a may include a first pair of circumferentially opposed (e.g., spaced about 180° from one another) slots 318a, 318b. However, the slots 318a, 318b may be spaced as desired. The slots 318a, 318b may extend through a thickness of a wall of the first trunk 316a such that the distal end region 304a includes a first arm 332a and a second arm 332b. The slots 318a, 318b may extend proximally from the distal end 314a of the leg 306a and terminate distal to a proximal end of the first trunk 316a. The first leg 306a may further include a first slit 320a extending through a laterally outward LOA sidewall thereof. The first slit 320a may be spaced about 90° from the first pair of slots 318a, 318b. The first slit 320a may extend less than an entire length of the first trunk 316a. For example, the first slit 320a may extend from a proximal end of the first trunk 316a to a point proximal of the distal end 314a of the first trunk 316a. In some cases, the first slit 320a may extend to and meet with the first notch extending through the first projection 302a, although this is not required. In other examples, the slit 320a may extend a full length of the first trunk 316a (e.g., from the distal end 314a to a proximal end of the first trunk 316a). While not explicitly shown, the first trunk 316a may include another slit similar in form and function to slit 320a positioned within a laterally inward LIA surface thereof. The first trunk 316a may further include a third slot 334a. The slot 334a may extend at a non-parallel and a non-orthogonal angle to the longitudinal axis of the anchor member 300 to partially define the second proximal surface 324b of the second projection 302b.

The second leg 306b may also include a second pair of circumferentially opposed (e.g., spaced about 180° from one another) slots 318c, 318d. However, the slots 318c, 318d may be spaced as desired. The slots 318c, 318d may extend through a thickness of a wall of the second trunk 316b such that the distal end region 304b includes a third arm 332c and a fourth arm 332d. The slots 318c, 318d may extend proximally from the distal end 314b of the leg 306b and terminate distal to a proximal end of the second trunk 316b. The second leg 306b may further include a second slit 320a extending through a laterally outward LOB sidewall thereof. The second slit 320a may be spaced about 90° from the first pair of slots 318. The first slit 320a may extend less than an entire length of the second trunk 316b. For example, the second slit 320a may extend from a proximal end of the second trunk 316b to a point proximal of the distal end 314b of the second trunk 316b. In some cases, the second slit 320a may extend to and meet with the second notch 328b extending through the third projection 302c, although this is not required. In other examples, the slit 320b may extend a full length of the second trunk 316b (e.g., from the distal end 314b to a proximal end of the second trunk 316b). While not explicitly shown, the second trunk 316b may include another slit similar in form and function to slit 320b positioned within a laterally inward LIB surface thereof. The second trunk 316b may further include a sixth slot 334b. The slot 334b may extend at a non-parallel and a non-orthogonal angle to the longitudinal axis of the anchor member 300 to partially define the fourth proximal surface 324d of the fourth projection 302d.

Referring to FIG. 16B, an inner surface of the distal end 314a of the first trunk 316a may include a taper or bevel 336a. For example, the wall thickness may decrease in a distal direction. The bevel 336a may extend about an entirety of the circumference of the first trunk 316a, although this is not required. For example, the wall thickness may decrease in a distal direction. Similarly, an inner surface of the distal end 314b of the second trunk 316b may include a taper or bevel 336b. For example, the wall thickness may decrease in a distal direction. The bevel 336b may extend about an entirety of the circumference of the second trunk 316b, although this is not required. The bevels 336a, 336b may be sized and shaped to generally conform to the proximal taper of the enlarged distal end regions 289a, 289b of the piercing elements 271a, 271b. This may facilitate proximal retraction of the enlarged distal end regions 289a, 289b of the piercing elements 271a, 271b relative to the anchor member 300. As the piercing elements 271a, 271b are proximally retracted the first and second arms 332a, 332b and the third and fourth arms 332c, 332d are radially deformed or expanded by the enlarged distal end regions 289a, 289b, as shown in FIGS. 13 and 14. For instance, the first and second arms 332a, 332b and the third and fourth arms 332c, 332d may be plastically deformed in a splayed configuration, as shown in FIGS. 13 and 14. The first and second slits 320a, 320b may also allow the lumens 310a, 310b of the first and second trunks 316a, 316b to expand such that the enlarged distal regions 289a, 289b may be proximally retracted therethrough, as discussed above regarding FIGS. 13-14. In the plastically deformed, splayed configuration, the distal ends of the first and second arms 332a, 332b and the third and fourth arms 332c, 332d may extend radially outward to a greater extent than the diameter of the enlarged distal end regions 289a, 289b, and thus greater than the diameter of the bore holes formed by the piercing elements 271, 271b into the bone.

Figure 17:
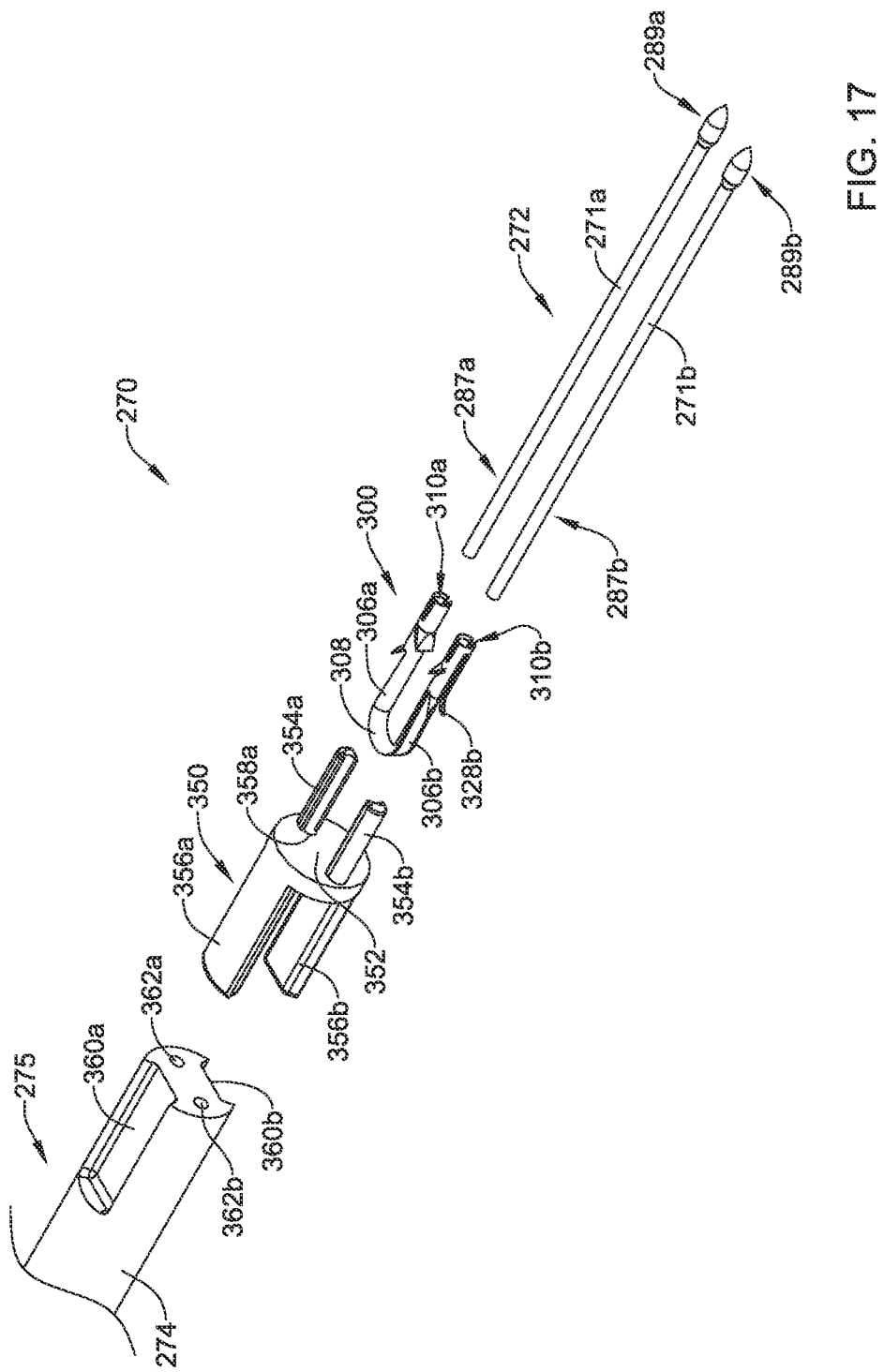
FIGS. 17-22 are perspective views illustrating a method of assembling the bone punch and anchor member delivery system with the anchor member of FIGS. 16A-16B.

FIGS. 17-22 illustrate a perspective view of a method for assembling the bone punch and anchor member delivery system 270. FIG. 17 illustrates an exploded perspective view of a distal end region of the bone punch and anchor member delivery system 270. Generally, the distal end region of the bone punch and anchor member delivery system 270 may include a distal end region 275 of the elongate shaft 274, a cap member 350, the anchor member 300, and the piercing tip 272. The cap member 350 may include a central disc-shaped body portion 352. A first prong 354a and a second prong 354b extend distally from a distal surface of the body portion 352. The first and second prongs 354a, 354b may have a generally concave laterally inward surface configured to generally conform to the generally convex laterally outward surface of the piercing elements 271a, 271b. The first prong 354a may be positioned about a first aperture 358a. The first aperture 358a extends through an entirety of a thickness of the body portion 352. While not explicitly shown, a second aperture extending through a thickness of the body portion is similarly positioned adjacent to the second prong 354b. A first arm 356a and a second arm 356b extend proximally from a proximal surface of the body portion 352. The first and second arms 356a, 356b may be radially spaced from one another about the circumference of the body portion 352. In some cases, the first and second arms 356a, 356b may be positioned across from one another, although this is not required. The first and second arms 356a, 356b are sized and shaped to be received within mating recesses 360a, 360b in the distal end region 275 of the elongate shaft 274. The recesses 360a, 360b may extend radially inwards from a lateral outer surface of the elongate shaft 274 towards a central longitudinal axis of the elongate shaft 274. The elongate shaft 274 may further include a first lumen 362a and a second lumen 362b extending proximally from a distal surface thereof. The first and second lumens 362a, 362 may extend generally parallel to one another and generally parallel to the longitudinal axis of the elongate shaft 274. The first and second lumens 362a, 362 may extend over less than an entire length of the elongate shaft 274 or over then entire length, as desired.

Figure 18:
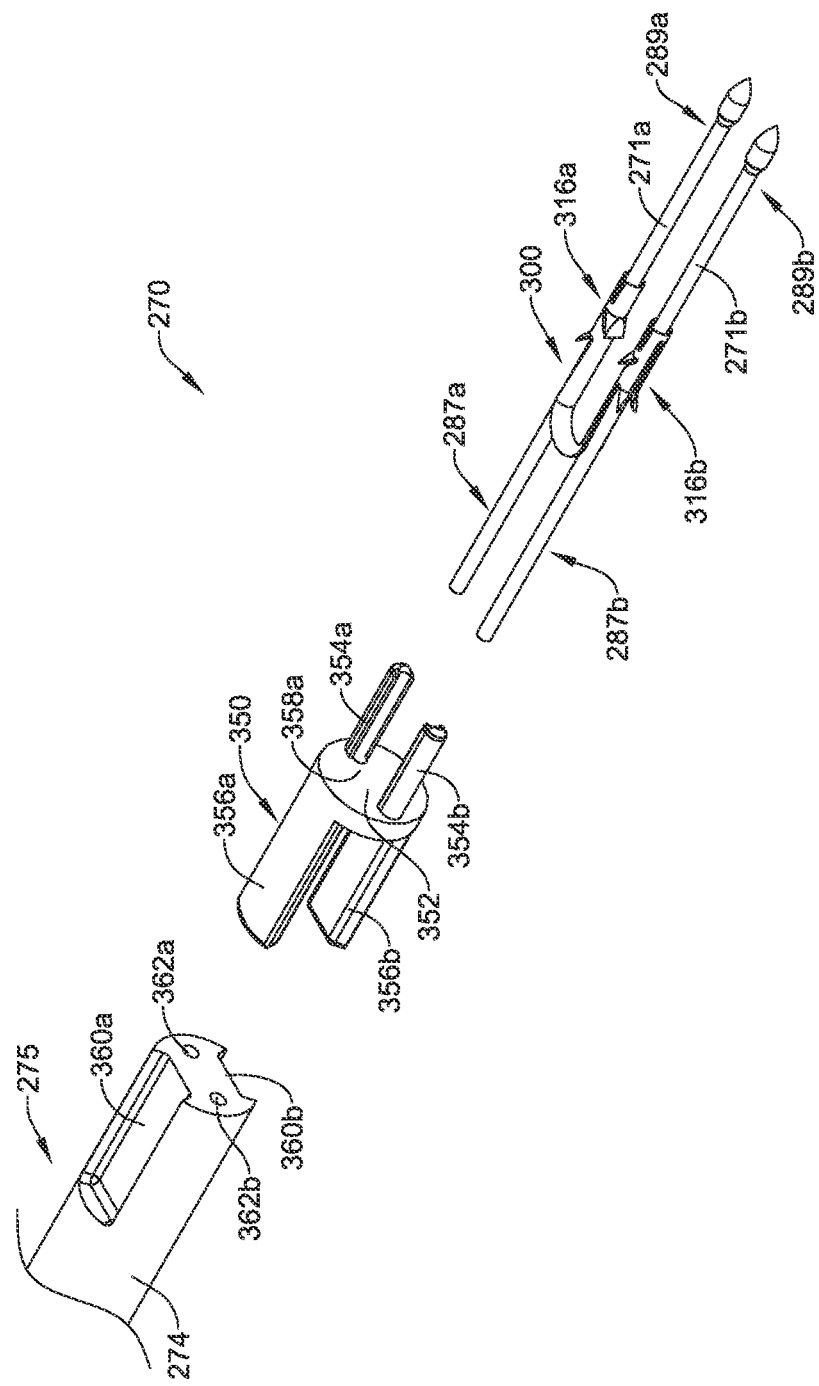
Figure 19:
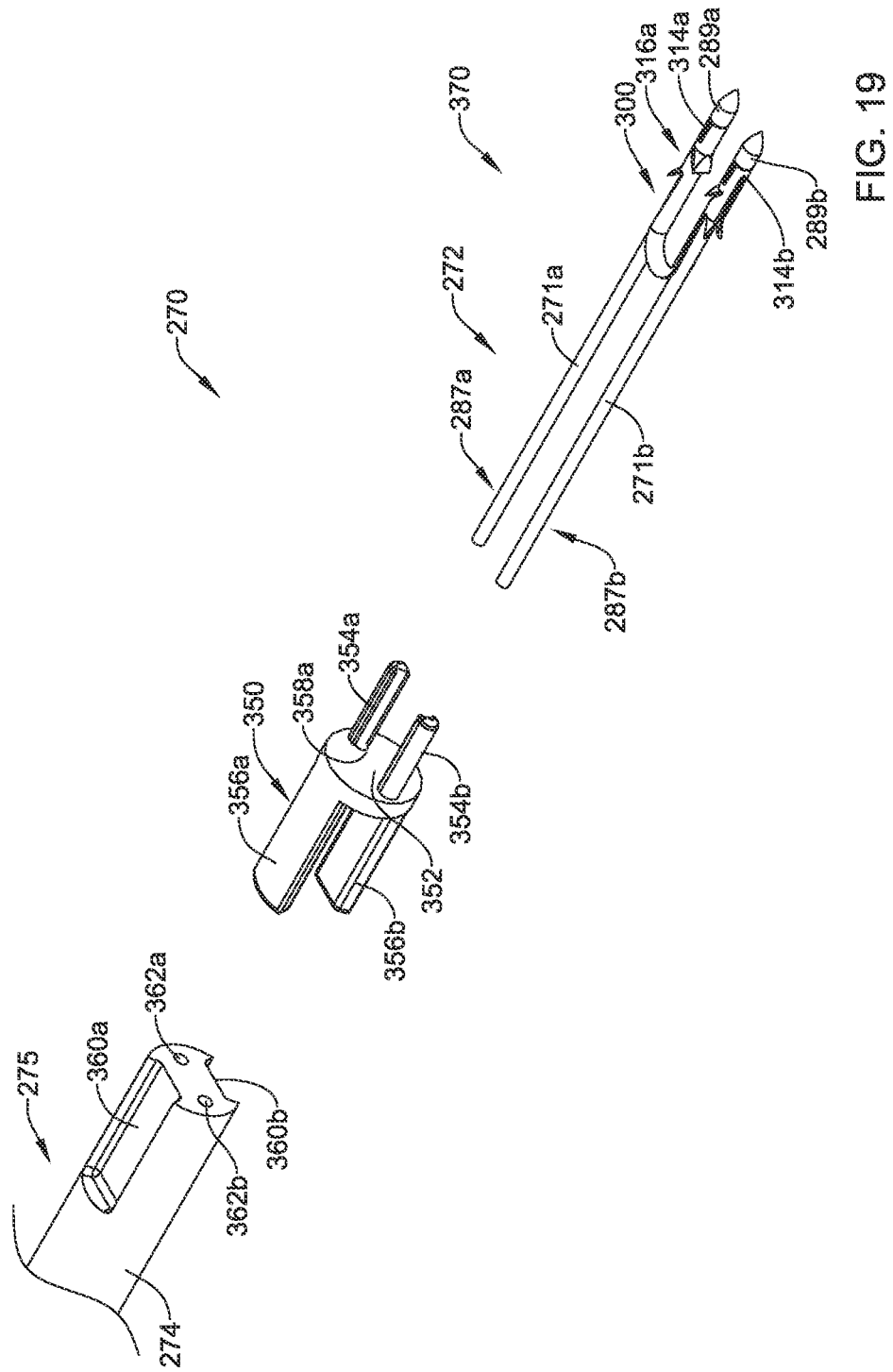

To begin assembly of the bone punch and anchor member delivery system 270, first the anchor member 300 is slid over the proximal end regions 287a, 287b of the piercing elements 271a, 271b. More particularly, the distal opening of the lumens 310a, 310b of the first and second trunks 316a, 316b are positioned over the proximal end regions 287a, 287b of the piercing elements 271a, 271b and slid distally along a length thereof, as shown in FIG. 18. While the method of assembling is described as the anchor member 300 moving along the piercing tip 272, the piercing tip 272 may also be considered to move relative to the anchor member 300. For example, it may be that the proximal end regions 287a, 287b of the piercing elements 271a, 271b are inserted into the distal opening of the lumens 310a, 310b of the first and second trunks 316a, 316b and proximally moved therethrough. The anchor member 300 is advanced along the piercing elements 271a, 271b until the distal ends 314a, 314b of the first and second trunks 316a, 316b contact the enlarged distal end regions 289a, 289b of the piercing elements 271a, 271b to form a first subassembly 370, as shown in FIG. 19. Said differently, advancement of the anchor member 300 along the piercing tip 272 may be limited by a mechanical interaction between an enlarged distal end region 289a, 289b of the piercing elements 271a, 271b or piercing tip 272 and a distal end 314a, 314b of the anchor member 300 such that the piercing tip 272 extends distal to the anchor member 300. Thus, the distal ends 314a, 314b of the first and second trunks 316a, 316b may abut the enlarged distal end regions 289a, 289b to prevent further distal advancement of the anchor member 300 relative to the piercing tip 272.

Figure 20:
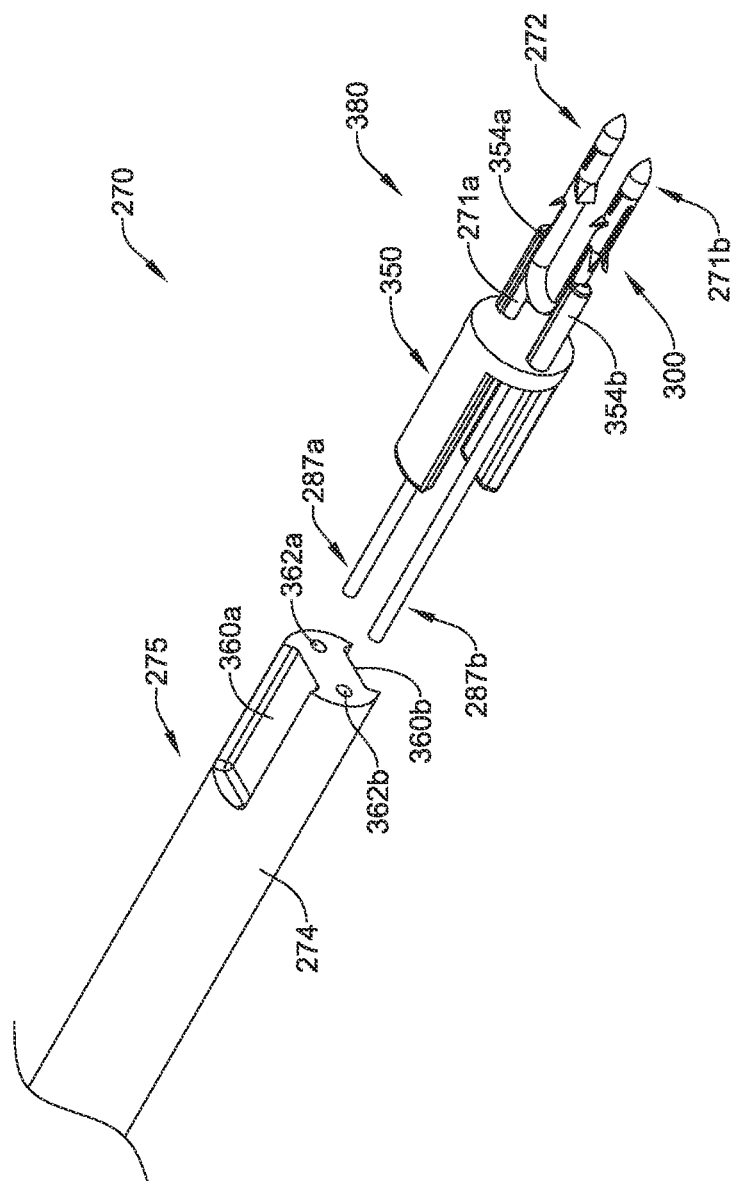

The first subassembly 370 is then assembled with the cap member 350, as shown in FIG. 20. For example, the proximal end regions 287a, 287b of the piercing elements 271a, 271b may be inserted and advanced proximally through the first and second apertures 358a of the body portion 352 of the cap member 350, to form a second subassembly 380. Alternatively, the cap member 350 may be distally advanced over the piercing elements 271a, 271b. Once the first subassembly 370 is in a desired positioned or configuration relative to the cap member 350, the cap member 350 and the first subassembly 370 may be fixedly secured to one another. For example, the piercing elements 271a, 271b may be welded, soldered, brazed, adhered, etc. to the cap member 350. In some cases, the proximal surface of the body portion 352 of the cap member 350 may include a recess such that the piercing elements 271a, 271b may be secured to the cap member 350 without creating a bulge or protrusions extending from the proximal surface of the body portion 352. When assembled with the first subassembly, the first and second prongs 354a, 354b may extend axially along a portion of the piercing elements 271a, 271b. As described above, the laterally inward surface of the prongs 354a, 354b may generally conform to the laterally outward surface of the piercing elements 271a, 271b. The prongs 354a, 354b may provide additional strength to the piercing tip 272 as the piercing tip 272 is being driven into the tissue and/or bone.

Figure 21:
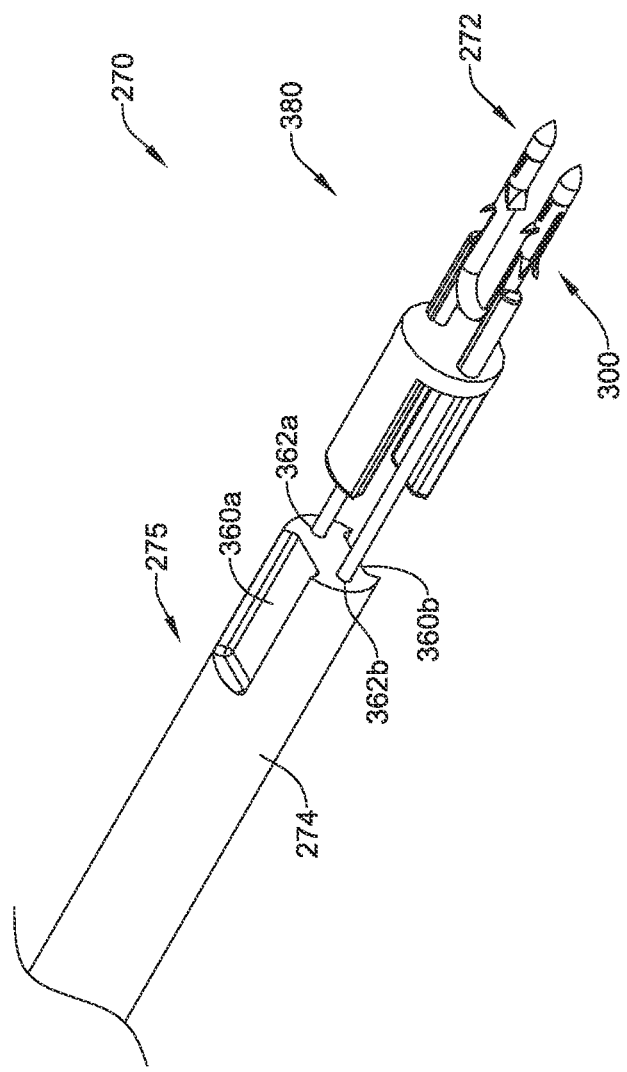
Figure 22:
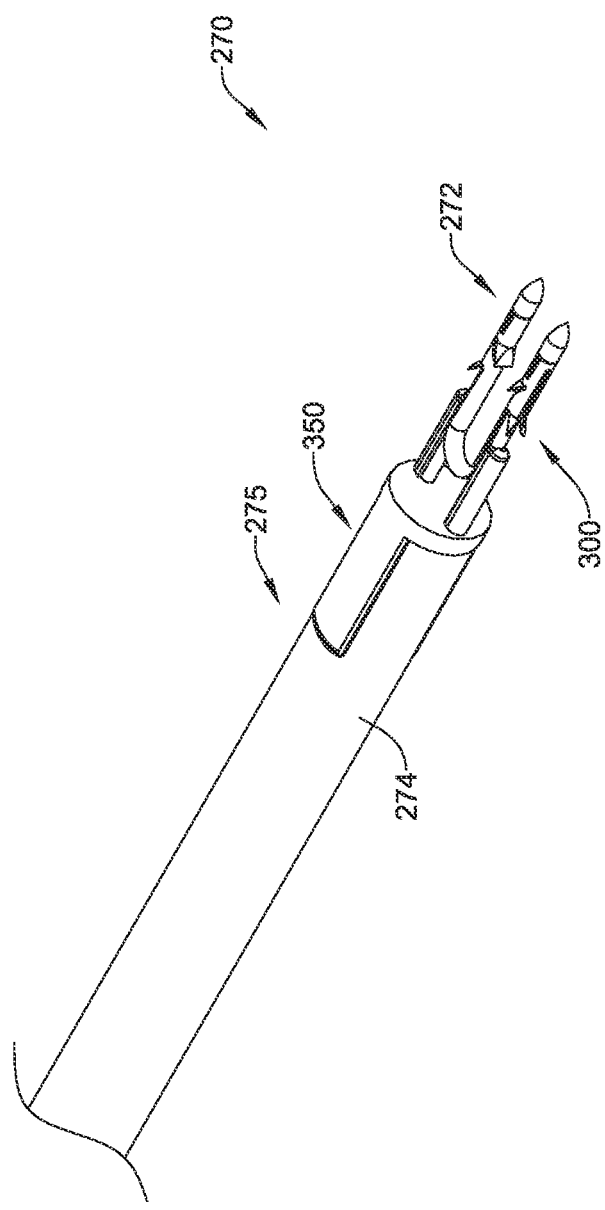

Once the second subassembly 380 is assembled, the cap member 350 may then be attached to the distal end region 275 of the elongate shaft 274. First, the proximal end regions 287a, 287b of the piercing elements 271a, 271b may be inserted into the lumens 362a, 362b of the elongate shaft 274, as shown in FIG. 21. Then, the second subassembly 380 is moved proximally relative to the elongate shaft 274 until the first and second arms 356a, 356b of the cap member 350 are received within the recesses 360a, 360b of the elongate shaft 274, as shown in FIG. 22. However, in some cases, the cap member 350 may not include the proximally extending arms 356a, 356b. In such an instance, the second subassembly 380 is moved proximally relative to the elongate shaft 274 until the proximal surface of the body portion 352 is in contact with a distal end of the elongate shaft 274. The cap member 350 may then be fixedly secured to the elongate shaft 274 by welding, brazing, soldering, adhering, etc.

Figure 23:
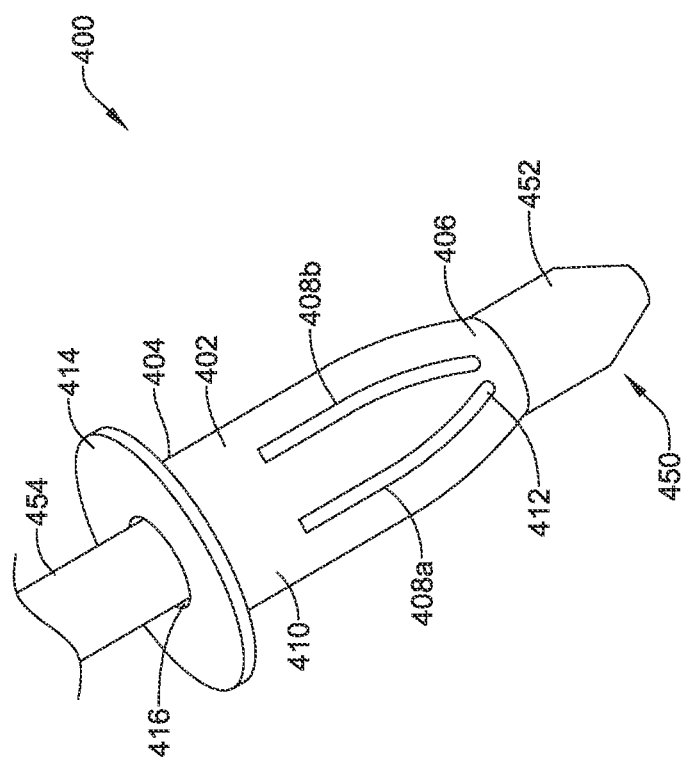
FIG. 23 is a perspective view of another illustrative anchor member in a delivery configuration.

FIG. 23 is a perspective view of another illustrative anchor member 400 disposed on a piercing element 450. The piercing element 450 may be similar in form and function to the piercing elements 271a, 271b described herein. The anchor member 400 may include a generally tubular body 402 extending from a proximal end 404 to a distal end 406. The body 402 may include a plurality of slits 408a, 408b (collectively, 408) spaced about a circumference of the body 402. While two slits 408a, 408b are illustrated it is contemplated that additional slits may be provided about the circumference of the body 402. The body 402 may include any number of slits desired, such as, two, three, four, five, six, or more. The slits 408 may be uniformly or eccentrically positioned about the circumference of the body 402, as desired. The slits 408 may extend over less than an entire length of the body 402 such that in the delivery configuration the body 402 includes a continuous proximal ring 410 and a continuous distal ring 412. The anchor member 400 may further include an annular proximal head 414. The proximal head 414 may have a cross-sectional dimension that is greater than the body 402. A lumen 416 may extend through an entirety of the anchor member 400.

The anchor member 400 may be configured to be delivered to a tissue or bone at a same time as a hole is created. The anchor member 400 may be loaded onto the piercing element 450 in a similar manner to the anchor member 300 described above. The piercing element 450 may have an enlarged distal end region 452 that has a diameter greater than a proximal region 454 of the piercing element 450. This may allow the anchor member 400 to be loaded over the piercing element 450. The enlarged distal end region 452 may have a dimeter that is greater than a diameter of the distal ring 412. This may create a mechanical stop between the anchor member 400 and the piercing element 450. The anchor member 400 may be delivered to the tissue or bone as described with respect to FIGS. 12-14.

Figure 24:
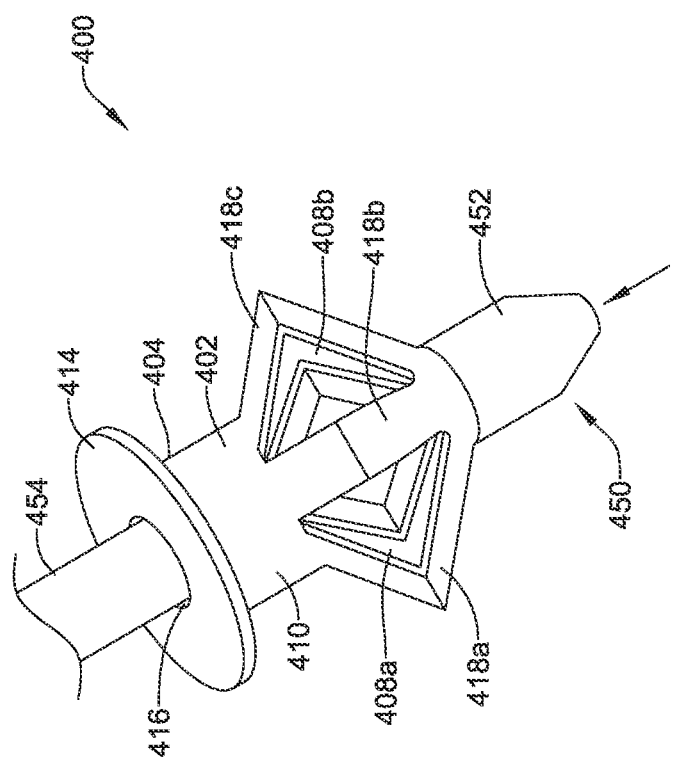
FIG. 24 is a perspective view of the illustrative anchor member of FIG. 23 in a partially deployed configuration.
Figure 25:
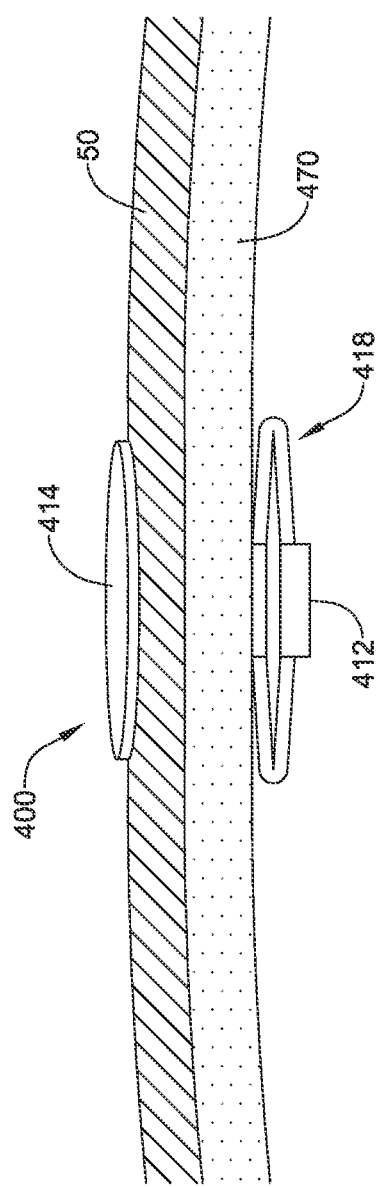
FIG. 25 is a partial cross-sectional view of the illustrative anchor member of FIG. 23 in a deployed configuration.

Once the anchor member 400 has penetrated the tissue or bone, the piercing element 450 may be proximally retracted. As the piercing element 450 is proximally retracted, the distal ring 412 of the body 402 may be proximally displaced with the piercing element 450 due to the mechanical engagement between the anchor member 400 and the piercing element 450. This may cause the expanding members 418a, 418b, 418c (collectively, 418) to radially deform, as shown in FIG. 24, which illustrates the anchor member 400 in a partially deployed configuration. The expanding members 418 may be the strips of the body 402 between adjacent slits 408. As the length of the expanding members 418 is decreased, the expanding members 418 may bend or deform such that the body 402 has a greater cross-sectional dimension at over a region adjacent to the slits 408 than at the proximal or distal rings 410, 412. Deformation of the body 402 to a greater cross-sectional dimension may result in plastic deformation of the body 402, such that the body 402 retains a radially enlarged configuration. Proximal actuation of the piercing element 450 may continue to shorten a length of the body 402 until a proximal portion of the expanding members 418 is in contact with a cortical shell 470 of the bone and a distal portion of the expanding members 418 is in contact with the proximal portion, as shown in FIG. 25, which illustrates the anchor member 400 in a deployed configuration. To fully retract the piercing element 450, the distal ring 412 may be configured to snap, break, or expand. As shown in FIG. 25, the anchor member 400 may be deployed such that the proximal head 414 is positioned on an outer surface of an implant 50 while the body portion is 402 is substantially within the tissue in its plastically deformed, expanded configuration. The proximal ring 410 may extend through the implant and the cortical shell 470 of the bone. The enlarged diameter of the proximal head 414 prevents the anchor member 400 from fully entering the tissue or bone while the increased diameter of the expanding members 418 prevents the anchor member 400 from exiting the tissue or bone.

Figure 26A:
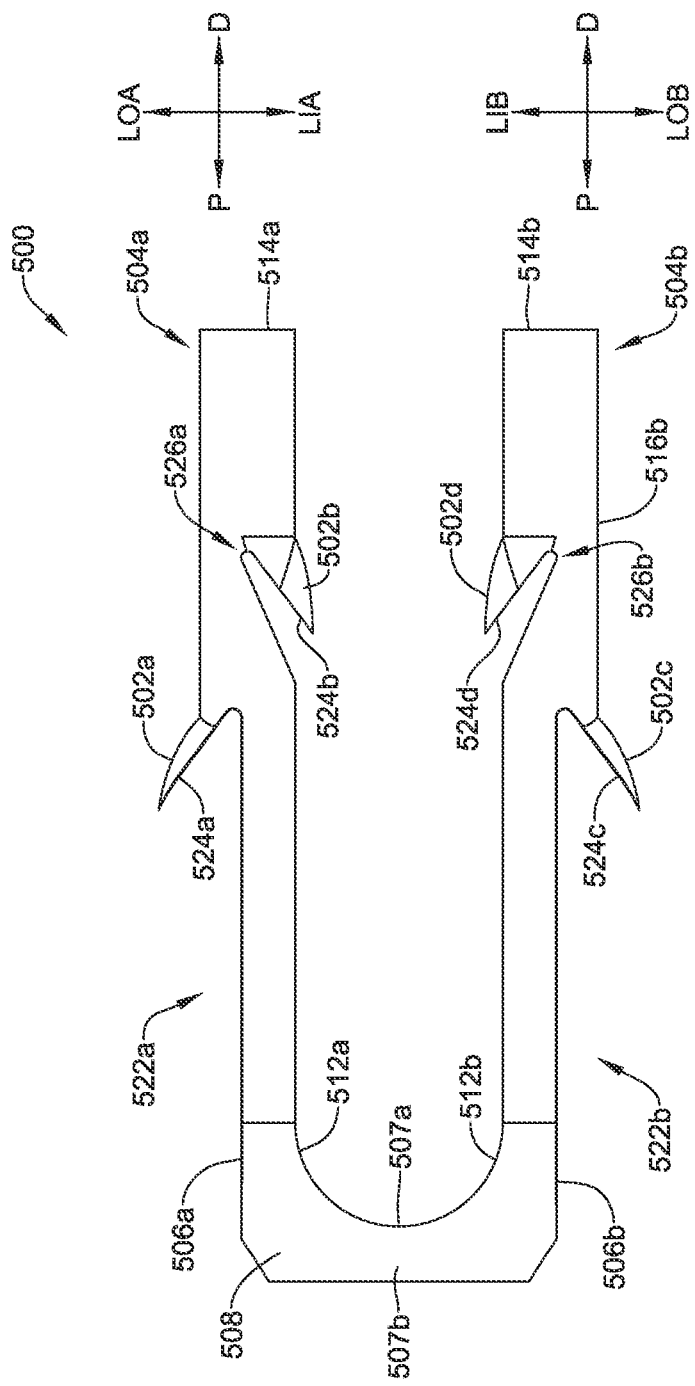
FIG. 26A is a side view of another illustrative anchor member.
Figure 26B:
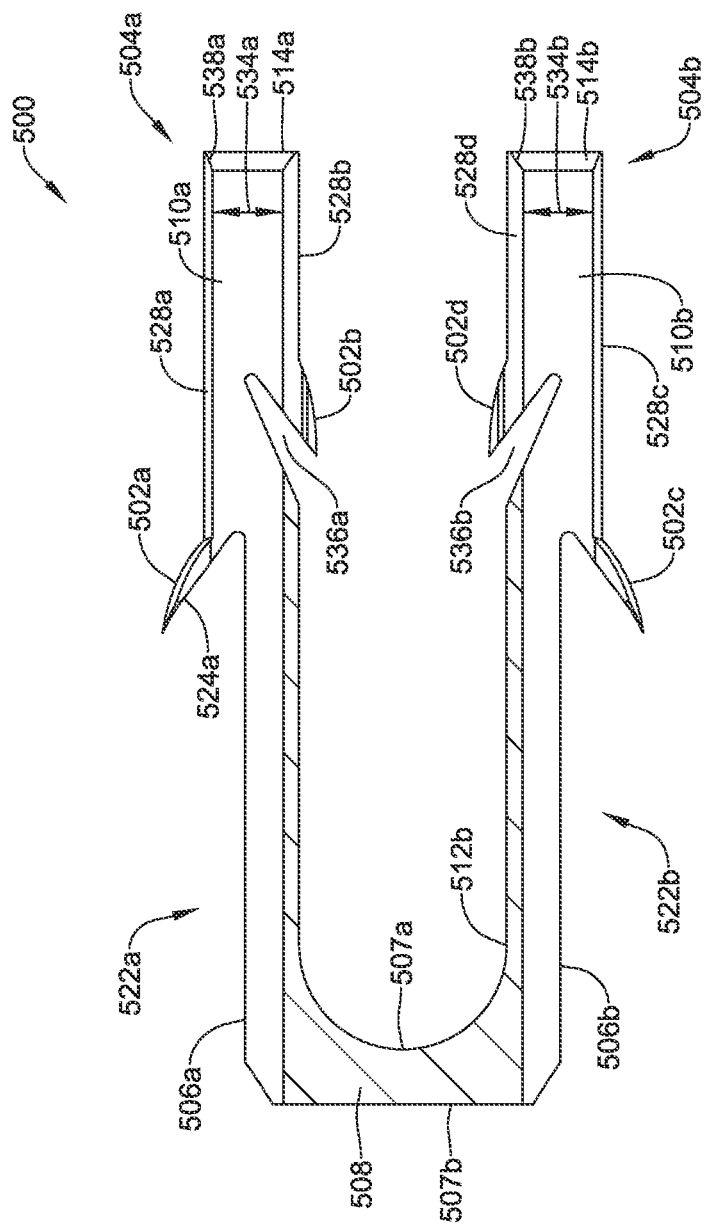
FIG. 26B is a cross-sectional view of the illustrative anchor member of FIG. 26A.
Figure 26C:
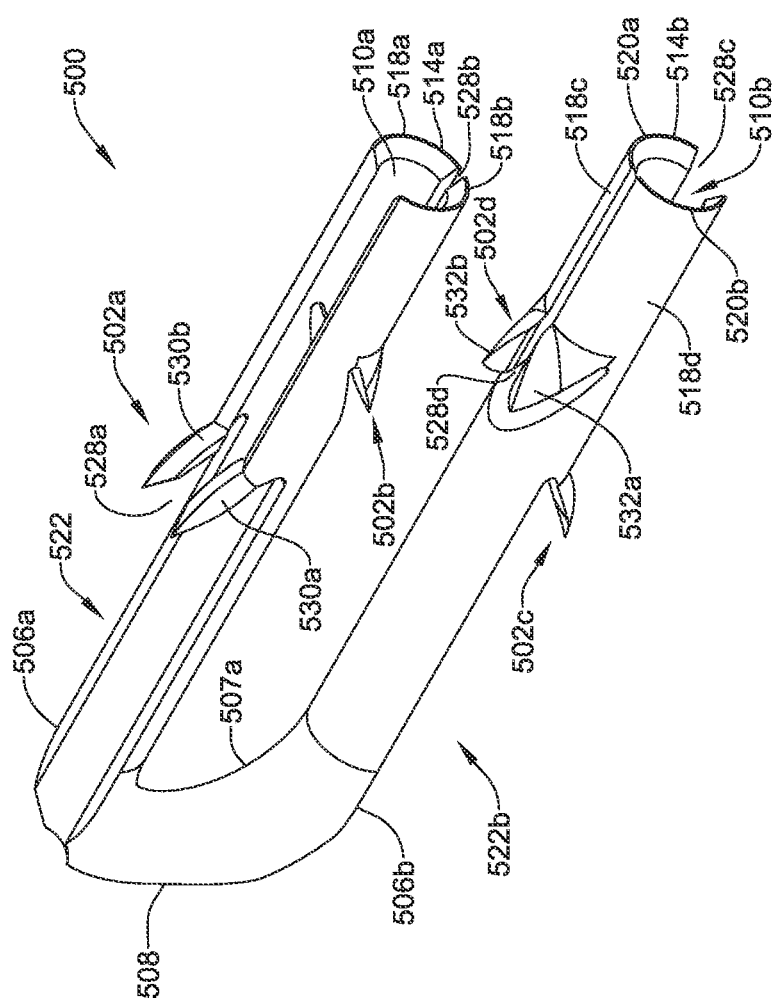
FIG. 26C is a perspective view of the illustrative anchor member of FIG. 26A.

FIG. 26A illustrates a side view of another illustrative anchor member 500 (e.g., staple), FIG. 26B illustrates a cross-sectional view of the anchor member 500, and FIG. 26C illustrates a perspective view of the anchor member 500. It is contemplated that the anchor member 500 may be delivered to the body with the bone punch and anchor member delivery system 270 described above. Alternatively, or additionally, the anchor member 500 may be delivered with an alternative bone punch and anchor member delivery system 550 (see, for example, FIGS. 27-30) which may be similar in form and function to the bone punch and anchor member delivery system 270. While the bone punch and anchor member delivery system 550 may include some structural differences, the bone punch and anchor member delivery system 550 may be used in a similar manner to the bone punch and anchor member delivery system 270 described herein. Although the various parts of the exemplary anchor member 500 are depicted in relative proportion to other parts of the anchor member 500, other configurations in size and orientation of the various parts are also contemplated in other examples. A number of reference directions are illustrated using arrows in FIG. 26A to assist in understanding the details of the anchor member 500. The illustrated directions include: proximal direction P, distal direction D, first laterally outward direction LOA, second laterally outward direction LOB, first laterally inward direction LIA, and second laterally inward direction LIB. In some instances, the anchor member 500 may be a monolithic structure formed of a polymer material, such as polyetheretherketone (PEEK), or a metallic material, such as stainless steel or nitinol. In other instances, the anchor member 500 may include portions formed of a combination of multiple materials.

In some examples, the anchor member 500 comprises a first leg 506a, a second leg 506b, and a bridge portion 508 extending between and connecting the first leg 506a and the second leg 506b. The bridge 508 may have a generally curved distal portion or surface 507a and a generally planar proximal portion or surface 507b. However, this is not required. In some cases, the proximal portion 507b may be curved similar to the bridge 30 described herein. The bridge 508 may abut and/or extend between and connect the proximal end 512a of the first leg 506a and the proximal end 512b of the second leg 506b. The first leg 506a may include a first trunk 516a, with the first trunk 516a generally having a greater width than the rest of the first leg 506a (e.g., a non-trunk portion 522a) as depicted in FIGS. 26A, 26B, and 26C. In some examples, the first trunk 516a may be generally tubular and define a lumen 510a extending therethrough. The length of the first trunk 516a relative to the overall length of the first leg 506a can vary in different examples. For instance, the first trunk 516a can extend for the entire length of the first leg 506a such that the bridge 508 abuts with or is adjacent to the first trunk 516a. When present, the non-trunk portion 522a may have a generally concave shape configured to conform to a convex outer surface of a proximal end region of a first piercing element 271a, 560a. For example, the non-trunk portion 522a may have a concave surface facing laterally outwardly to face or be juxtaposed with the convex outer surface of the proximal end region of the first piercing element 271a, 560a.

Similarly, the second leg 506b may include a second trunk 516b, with the second trunk 516b generally having a greater width than the rest of the second leg 506b (e.g., a non-trunk portion 522b). Additionally, the second trunk 516b may extend for at least a portion of the second leg 506b. In some examples, the second trunk 516b may be generally tubular and define a lumen 510b extending therethrough. The length of the second trunk 516b relative to the overall length of the second leg 506b can vary in different examples. For instance, the second trunk 516b can extend for the entire length of the second leg 506b such that the bridge 508 abuts with or is adjacent to the second trunk 516b. When present, the non-trunk portion 522b may have a generally concave shape configured to conform to a convex outer surface of a proximal end region of the second piercing element 271b, 560b. For example the non-trunk portion 522b may have a concave surface facing laterally outwardly to face or be juxtaposed with a convex outer surface of a proximal end region of a second piercing element 560b. In FIGS. 26A, 26B, and 26C, the first trunk 516a and the second trunk 516b are shown extending distally from a proximal portion of the first leg 506a and the second leg 506b, respectively.

In the example of FIGS. 26A, 26B, and 26C, the first trunk 516a has a lateral extent, or cross-sectional area, that is larger than a lateral extent of the non-trunk portion 522a of the first leg 506a and the bridge 508. The anchor member 500 may include a first change in lateral stiffness disposed where the distal end of the non-trunk portion 522a of the first leg 506a abuts the first trunk 516a. As depicted, the change in the lateral extent and thus the change in stiffness is abrupt, but can be gradual in alternative examples—such as through a gradual change in lateral extent between the first trunk 516a and the non-trunk portion 522a. In an example where the first trunk 516a extends for the full length of the first leg 506a, the change in stiffness may occur where the first trunk 516a abuts the bridge 508. With reference to the example of FIGS. 26A, 26B, and 26C, it will be appreciated that the first trunk 516a is mounted eccentrically to the first leg 506a and the second trunk 516b is mounted eccentrically to the second leg 506b. As with the first trunk 516a, the second trunk 516b has a lateral extent, or cross-sectional area that is larger than a lateral extent of the non-trunk portion 522b of the second leg 506b and the bridge 508. The anchor member 500 may include a second change in lateral stiffness where the distal end of the non-trunk portion 522b of the second leg 506b abuts the second trunk 516b. Similarly to the first leg 506a, in some examples, the change in stiffness may be abrupt or gradual. If the second trunk 516b extends for the entire length of the second leg 506b, the change in stiffness may occur at the abutment with the bridge 508. In additional examples where there may be no change in lateral extent between the first and second trunks 516a, 516b and the first and second legs 506a, 506b, respectively, a change in stiffness may be accomplished by the use of different materials for the first and second trunks 516a, 516b and the first and second legs 506a, 506b.

Some examples of the anchor member 500 may include at least a first projection or barb 502a and a second projection or barb 502b on the first trunk 516a longitudinally spaced apart from one another, and a third projection or barb or barb 502c and a fourth projection 502d on the second trunk 516b longitudinally spaced apart from one another. The first and third projections 502a, 502c on the first and second trunks 516a, 516b, respectively, may further include a first proximal surface 524a and a third proximal surface 524c, respectively, each extending away from its respective trunk in a first direction, such as out and away from each opposite trunk 516a, 516b. The first direction may be a direction such that the first and third proximal surfaces 524a, 524c will engage with tissue or bone after the trunk is inserted therein and by natural movement of the tissue or bone. In some examples, a pullout force may be applied to the bridge 508 to further engage the first and third proximal surfaces 524a, 524c with the bone or tissue. The natural movement of the bone or tissue or the pullout force creates a first moment centered on the area of reduced stiffness adjacent each trunk 516a, 516b, tending to rotate each trunk 516a, 516b thereabout. The rotation of each trunk 516a, 516b may further provide a greater holding force of the anchor member 500 in bone or tissue. The second projection 502b and the fourth projection 502d on the first and second trunks 516a, 516b, respectively, may include a second proximal surface 524b and a fourth proximal surface 524d, respectively, extending away from its respective trunk in a second direction, different from the first direction, such as inward, toward the opposite trunk. For example, the second direction may be selected such that the second and fourth proximal surfaces 524b, 524d will engage tissue or bone after each trunk is inserted therein and by natural movement of the tissue or bone. In some examples, a pullout force may be applied to the bridge 508. A slit or area of reduced cross-section in each trunk adjacent the second and fourth projections 502b, 502d provide an area of weakness so that a second moment is applied to the trunk in response to natural movement of the tissue or bone and/or to a pullout force on the bridge 508. This moment causes rotation of the trunk 516a, 516b about the area of weakness and increases the holding force of the anchor member 500.

As illustrated in the example of the anchor member 500 in FIGS. 26A, 26B, and 26C, the first trunk 516a includes the first projection 502a disposed at a laterally outer side LOA of the first trunk 516a and the second projection 502b disposed at a laterally inner side LIA of the first trunk 516a. The first projection 502a includes the first proximal surface 524a extending away from the first trunk 516a in the first direction. With reference to FIGS. 26A, 26B, and 26C, it will be appreciated that the first direction has an outward lateral component and a proximal component so that the first proximal surface 524a extends outwardly and proximally away from the first trunk 516a. For example, the first direction may be selected such that the first proximal surface 524a will engage tissue or bone proximate the outer side of the first trunk 516a after being inserted therein so that a first moment is applied to the first trunk 516a in response to natural movement of the tissue or bone and/or to a pullout force on the bridge 508. The moment centers on the arm portion of lesser stiffness adjacent the first projection 502a.

In the example of FIGS. 26A, 26B, and 26C, the first trunk 516a includes a first localized area of weakness 526a disposed proximate the second projection 502b. The second projection 502b includes the second proximal surface 524b extending away from the first trunk 516a in a second direction. The second direction is selected such that the second proximal surface 524b will engage tissue or bone proximate the inner side of the first trunk 516a when inserted therein so that a second moment is applied to the first trunk 516a in response to natural movement of the tissue or bone and/or a pullout force on the bridge 508. The moment centers around the first localized area of weakness 526a. The second moment has a direction that is generally opposite a direction of the first moment. It will be appreciated that the second direction has an inward lateral component and a proximal component so that the second proximal surface 524b extends inwardly and proximally away from the first trunk 516a. In other examples, the first leg 506a may not include the second projection 502b. In such examples, only a first moment may be applied to the first trunk 516a in response to natural movement of the tissue or bone and/or a pullout force on the bridge 508.

The second trunk 516b includes the third projection 502c disposed at an outer side LOB of the second trunk 516b and the fourth projection 502d disposed at an inner side LIB of the second trunk 516b. In the example of FIGS. 26A, 26B, and 26C, the third projection 502c includes a third proximal surface 524c extending away from second trunk 516b in a third direction. With reference to FIGS. 26A, 26B, and 26C, it will be appreciated that the third direction has an outward lateral component and a proximal component so that the third proximal surface 524c extends outwardly and proximally away from the second trunk 516b. The third direction is selected such that the third proximal surface 524c will engage tissue or bone proximate the outer side of the second trunk 516b when inserted therein so that a third moment is applied to the second trunk 516b in response to natural movement of the tissue or bone and/or a pullout force on bridge 508.

In the example of FIGS. 26A, 26B, and 26C, the second trunk 516b includes a second localized area of weakness 526b disposed proximate the fourth projection 502d. The fourth projection 502d includes a fourth proximal surface 524d extending away from the second trunk 516b in a fourth direction. In the example of FIGS. 26A, 26B, and 26C, the fourth direction is selected such that the second proximal surface 524b will engage tissue or bone proximate the inner side of the second trunk 516b when inserted therein so that a fourth moment is applied to the second trunk 516b in response to natural movement of the tissue or bone and/or a pullout force on the bridge 508. The fourth moment has a direction that is generally opposite a direction of the third moment. It will be appreciated that the fourth direction has an inward lateral component and a proximal component so that the fourth proximal surface 524d extends inwardly and proximally away from the second trunk 516b. In other examples, the second leg 506b may not include the fourth projection 502d. In such examples, only a first moment may be applied to the second trunk 516b in in response to natural movement of the tissue or bone and/or a pullout force on the bridge 508.

While not explicitly shown, in some embodiments, the anchor member 500 includes proximal projections that extend away from or outward from the bridge 508, while the distal projections extend inward or toward the center of the bridge 508. This creates generally opposing forces in response to tension on the bridge 508 which, in combination with areas of weakness or reduced lateral extent, substantially increases the holding force of the anchor member 500 in bone as the different portions of the trunks tend to rotate in opposite directions and apply force to an opposing wall in the hole in the bone in which the anchor member 500 is positioned. It is however, understood that other configurations of the projections are possible. In some examples, only two projections are included and they extend in different directions to cause different force responses as tension is applied to the bridge 508. Additional examples may include varying numbers of projections which produce one or more moments in each of the first and second legs 506a, 506b.

In some examples, each projection of the anchor member 500 may be divided (e.g., bifurcated) to form a plurality of points for greater retention in tissue or bone. In the example of FIGS. 26A, 26B, and 26C, the first projection 502a of the first trunk 516a defines a first notch or slot 528a that divides the first projection 502a into a first sub-projection 530a and a second sub-projection 530b. The second projection 502b of the second trunk 516b defines a second notch or slot 528b. The second notch or slot 528b may be similar in form and function to the first notch or slot. In the example of FIGS. 26A, 26B, and 26C, the second notch or slot 528b divides the second projection 502b into a first sub-projection and a second sub-projection (not explicitly shown). The third projection 502c of the second trunk 516b may a third notch or slot 528c that divides the third projection 502c into a first sub-projection and a second sub-projection (not explicitly shown) and the fourth projection 502d of the second trunk 516b may define a fourth notch or slot 528d that divides the fourth projection 502d into a first sub-projection 532a and a second sub-projection 532b, although this is not required.

With continued reference to FIGS. 26A, 26B, and 26C, the first trunk 516a defines a first lumen or cavity 510a and the second trunk 516b defines a second lumen or cavity 510b. The first lumen 510a extends into the first trunk 516a and the second lumen 510b extends into the second trunk 516b. The first and second lumens 510a, 510b are sized to cooperate with the piercing tip 556 for holding and inserting the staple into tissue or bone. As described above, the piercing tip 556 includes longitudinally extending piercing elements 560a, 560b that fit within (e.g., extend through) the first and second lumens 510a, 510b to hold the anchor member 500 and push it into position in the tissue or bone as the piercing elements 560a, 560b abuts a portion of its respective trunk. The first lumen 510a and the second lumen 510b may extend through the entire length of the first trunk 516a and the second trunk 516b, respectively, or other portions of the anchor member 500 in some examples. In some embodiments, the first lumen 510a and the second lumen 510b each have a generally circular or oblong cross-sectional shape to cooperate with a similarly shaped cross-section on the piercing elements 560a, 560b. However, the first lumen 510a and the second lumen 510b may have various cross-sectional shapes to cooperate with alternative staple delivery insert designs without deviating from the spirit and scope of the present disclosure. At least a portion of the first lumen 510a may extend laterally outward beyond the lateral outward extent of the bridge 508 and the non-trunk portion 522a. Likewise, at least a portion of the second lumen 510b may extend laterally outward beyond the lateral outward extent of the bridge 508 and the non-trunk portion 522b.

The first lumen 510a may have a first diameter or cross-sectional dimension 534a. The first diameter 534a may be greater than or approximately the same as an outer diameter of the proximal end region of the piercing element 271a, 560a such that the proximal end region freely slides within the first lumen 510a. The first diameter 534a may be less than the outer diameter of the enlarged distal end region of the piercing element 560a such that there is a mechanical engagement between the distal end 514a of the first leg 506a and the enlarged distal end region. This may limit undesired distal movement or deployment of the anchor member 500 relative to the piercing tip 556 or undesired proximal retraction of the piercing tip 556 relative to the anchor member 500. Furthermore, the outer diameter of the enlarged distal end region may be substantially similar (i.e., within 10%) to the outer lateral extent (e.g., outer diameter) of the first trunk 516a at its distal end such that the enlarged distal end region may form a bore hole large enough to receive the first trunk 516a therein (prior to radial expansion or plastic deformation of the first and second trunks 516a, 516b). For instance, the outer lateral extent (e.g., outer diameter) of the first trunk 516a may be equal to or less than the outer diameter of the enlarged distal end region, such as between 0-10% less than the diameter of the enlarged distal end region. Similarly, the second lumen 510b may have a second diameter or cross-sectional dimension 534b. The second diameter 534b may be approximately the same as the first diameter 534a and may be greater than or approximately the same as the outer diameter of the proximal end region of the piercing element 271b, 560b such that the proximal end region freely slides within the second lumen 510b. The second diameter 534b may be less than the outer diameter of the enlarged distal end region of the piercing element 560b such that there is a mechanical engagement between the distal end 514b of the second leg 506b and the enlarged distal end region. This may limit undesired distal movement or deployment of the anchor member 500 relative to the piercing tip 556 or undesired proximal retraction of the piercing tip 556 relative to the anchor member 500. Furthermore, the outer diameter of the enlarged distal end region may be substantially similar (i.e., within 10%) to the outer lateral extent (e.g., outer diameter) of the second trunk 516b at its distal end such that the enlarged distal end region may form a bore hole large enough to receive the second trunk 516b therein (prior to radial expansion or plastic deformation of the first and second trunks 516a, 516b). For instance, the outer lateral extent (e.g., outer diameter) of the second trunk 516b may be equal to or less than the outer diameter of the enlarged distal end region, such as between 0-10% less than the diameter of the enlarged distal end region.

The anchor member 500 may include features which allow the anchor member 500 to be loaded onto the piercing tip 556 using a side loading approach, as will be described in more detail with respect to FIGS. 27-30. It is contemplated that these features may also allow the piercing tip 556 to be proximally retracted through the lumens 510a, 510b to deploy the anchor member 500 within the tissue or bone. The first and second trunks 516a, 516b may radially expand or be deformed to permit the enlarged distal end regions to be withdrawn proximally through the lumens 510a, 510b. In some instances, the retraction of the enlarged distal end regions through the lumens 510a, 510b may cause the first and second trunks 516a, 516b to undergo plastic deformation as the first and second trunks 516a, 516b radially expand. For example, the first and second trunks 516a, 516b may each include one or more slots, slits, or channels 528a, 528b, 528c, 528d (collectively, 528) extending partially or completely through a thickness of the wall of the first and second trunks 516a, 516b and that are configured to facilitate radial expansion of at least some regions of the first and second trunks 516a, 516b. In some cases, the slots 528 may extend an entire length of the first and second trunks 516a, 516b, although this is not required.

The first leg 506a may include a first pair of circumferentially opposed (e.g., spaced about 180° from one another) slots 528a, 528b. However, the slots 528a, 528b may be spaced as desired. The slots 528a, 528b may extend through a thickness of a wall of the first trunk 516a such that the distal end region 504a includes a first arm 518a and a second arm 518b. The slots 528a, 528b may extend proximally from the distal end 514a of the leg 506a and terminate at or distal to a proximal end of the leg 506a, separating the first arm 518a from the second arm 518b along the length of the slots 528a, 528b. For example, the slots 528a, 528b may extend through the first and second projections 502a, 502b such that the slots 528a, 528b extend proximal of the first and second projections 502a, 502b. The slot 528a may extend along an entire length of the first trunk 516a to open laterally into the lumen 510a. The first trunk 516a may further include a third slot 536a. The slot 536a may extend at a non-parallel and a non-orthogonal angle to the longitudinal axis of the anchor member 500 to partially define the second proximal surface 524b of the second projection 502b.

The second leg 506b may also include a second pair of circumferentially opposed (e.g., spaced about 180° from one another) slots 528c, 528d. However, the slots 528c, 528d may be spaced as desired. The slots 528c, 528d may extend through a thickness of a wall of the second trunk 516b such that the distal end region 504b includes a third arm 518c and a fourth arm 518d. The slots 528c, 528d may extend proximally from the distal end 514b of the leg 506b and terminate at or distal to a proximal end of the second leg 506b, separating the third arm 518c from the fourth arm 518d along the length of the slots 528c, 528d. For example, the slots 528c, 528d may extend through the third and fourth projections 502c, 502d such that the slots 528c, 528d extend proximal of the third and fourth projections 502c, 502d. The slot 528c may extend along an entire length of the second trunk 516b to open laterally into the lumen 510b. The second trunk 516b may further include a sixth slot 536b. The slot 536b may extend at a non-parallel and a non-orthogonal angle to the longitudinal axis of the anchor member 500 to partially define the fourth proximal surface 524d of the fourth projection 502d.

Referring to FIG. 26B, an inner surface of the distal end 514a of the first trunk 516a may include a taper or bevel 538a. For example, the wall thickness may decrease in a distal direction. The bevel 538a may extend about an entirety of the circumference of the first trunk 516a, although this is not required. For example, the wall thickness may decrease in a distal direction. Similarly, an inner surface of the distal end 514b of the second trunk 516b may include a taper or bevel 538b. For example, the wall thickness may decrease in a distal direction. The bevel 538b may extend about an entirety of the circumference of the second trunk 516b, although this is not required. The bevels 538a, 538b may be sized and shaped to generally conform to the proximal taper of the enlarged distal end regions of the piercing elements 560a, 560b. This may facilitate proximal retraction of the enlarged distal end regions of the piercing elements 560a, 560b relative to the anchor member 500. As the piercing elements 560a, 560b are proximally retracted the first and second arms 518a, 518b and the third and fourth arms 518c, 518d are radially deformed or expanded by the enlarged distal end regions in a manner similar to that shown in FIGS. 13 and 14. For instance, the first and second arms 518a, 518b and the third and fourth arms 518c, 518d may be plastically deformed in a splayed configuration in a manner similar to that shown in FIGS. 13 and 14. While not explicitly shown, the first and second legs 516a, 516b may include additionally slits that further facilitate the expansion of the first and second trunks 516a, 516b. In the plastically deformed, splayed configuration, the distal ends of the first and second arms 518a, 518b and the third and fourth arms 518c, 518d may extend radially outward to a greater extent than the diameter of the enlarged distal end regions, and thus greater than the diameter of the bore holes formed by the piercing elements 560, 560b into the bone.

Figure 27:
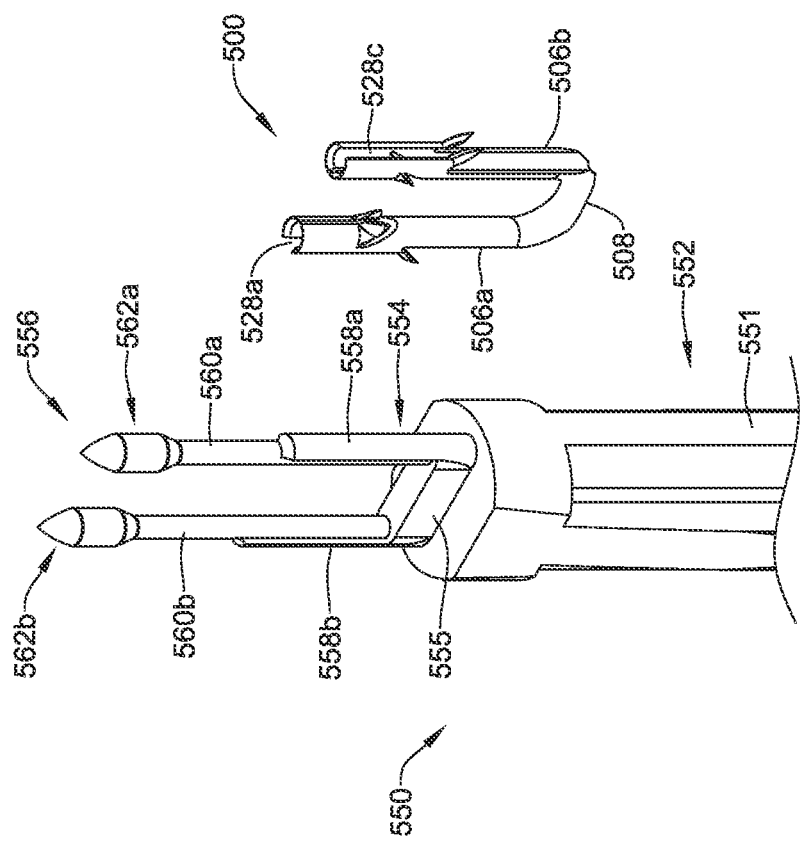

FIGS. 27-30 illustrate a perspective view of a method for assembling the bone punch and anchor member delivery system 550. FIG. 27 illustrates an exploded perspective view of a distal end region of the bone punch and anchor member delivery system 550. The bone punch and anchor member delivery system 550 may be similar in form and function the bone punch and anchor member delivery system 270. While the bone punch and anchor member delivery system 550 may include some structural differences, the bone punch and anchor member delivery system 550 may be used in a similar manner to the bone punch and anchor member delivery system 270 described herein. Generally, the distal end region of the bone punch and anchor member delivery system 550 may include a distal end region 552 of an elongate shaft 551, a cap member 554, the anchor member 500, and a piercing tip 556. The piercing tip 556 may be similar in form and function to the piercing tip 272 described herein. For example, the piercing tip 556 may include a first piercing element 560a and a second piercing element 560b each having an enlarged distal end region 562a, 562b.

The cap member 554 may include a central body portion 555. A first prong 558a and a second prong 558b extend distally from a distal surface of the body portion 556. The first and second prongs 558a, 558b may have a generally concave laterally inward surface configured to generally conform to the generally convex laterally outward surface of the piercing elements 560a, 560b. In some cases, the cap member 554 may be formed as a single monolithic structure with the elongate shaft 551. In other cases, the cap member 554 may be formed as a separate component and fixedly coupled to the elongate shaft 551. It is further contemplated that the elongate shaft 551 may be coupled to the piercing elements 560a, 560b using methods, such as, but not limited to overmolding. In other embodiments, the piercing elements 560a, 560b may be formed as a single monolithic structure with the elongate shaft 551.

To begin assembly of the bone punch and anchor member delivery system 550, first the first leg 506a of the anchor member 500 is coupled with the first piercing element 560a, as shown in FIG. 28. For example, the first laterally outward LOA side of the first leg 506a may be positioned against the first piercing element 560a such that the first slot 528a is adjacent to the first piercing element 560a. An applied lateral force (generally perpendicular to the longitudinal axis of the first piercing element 560a) may be used to snap the first leg 506a onto the first piercing element 560a from a lateral side of the first piercing element 560a. For example, the first slot 528a may allow the first and second arms 518a, 518b to temporarily flex to allow the first leg 506a to move laterally onto first piercing element 560a such that first leg 506a is positioned over (around) first piercing element 560a.

The anchor member 500 may then be rotated such that the second leg 506b is moved towards the second piercing element 560b, as shown in FIG. 29. It is contemplated that the anchor member 500 may be rotated in either direction and is not limited to the rotational direction illustrated in FIG. 29. Once the second laterally outward LOB side of the second leg 506b is adjacent to the second piercing element 560b, a lateral force (generally perpendicular to the longitudinal axis of the second piercing element 560b) may be applied to the second leg 506b to snap the second leg 506b onto the second piercing element 560b from a lateral side of the second piercing element 560b, as shown in FIG. 30. For example, the third slot 528c may allow the third and fourth arms 518c, 518d to temporarily flex to allow the second leg 506b to move laterally onto second piercing element 560b such that second leg 506b is positioned over (around) second piercing element 560b.

The materials that can be used for the various components of the medical device(s) and the various elements thereof disclosed herein may include those commonly associated with medical devices. For simplicity purposes, the following discussion refers to the apparatus. However, this is not intended to limit the devices and methods described herein, as the discussion may be applied to other elements, members, components, or devices disclosed herein, such as, but not limited to, the medical device, the housing assembly, the bone punch, the bone staple, and/or elements or components thereof.

In some embodiments, the apparatus, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRIL-AMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the apparatus, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the apparatus in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the apparatus to achieve the same result.

In some embodiments, a degree of Magnetic Resonance Imaging (MRI) compatibility is imparted into the apparatus and/or other elements disclosed herein. For example, the apparatus, and/or components or portions thereof, may be made of a material that does not substantially distort the image and create substantial artifacts (e.g., gaps in the image). Certain ferromagnetic materials, for example, may not be suitable because they may create artifacts in an MRI image. The apparatus, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the apparatus and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A delivery system for delivering an anchor member to a bone of a patient the system comprising:
    a bone punch including an elongate shaft, a head at a proximal end of the elongate shaft, and a piercing tip at a distal end of the elongate shaft, wherein the piercing tip is configured to be driven into the bone, wherein a distal end of the piercing tip includes an enlarged region having a diameter;
    an anchor member surrounding a proximal portion of the piercing tip extending proximal of the enlarged region with the enlarged region of the piercing tip extending distal of the anchor member;
    wherein the anchor member is configured to penetrate the bone of the patient in cooperation with the piercing tip;
    wherein the diameter of the enlarged region is greater than a diameter of the proximal portion of the piercing tip that the anchor member surrounds.

2. The system of claim 1, wherein the piercing tip comprises a first piercing element and a second piercing element extending parallel to the first piercing element.

3. The system of claim 1, wherein the diameter of the enlarged region of the piercing tip is greater than a diameter of a portion of the anchor member surrounding the proximal portion of the piercing tip.

4. The system of claim 3, wherein the anchor member comprises a staple having a first leg, a second leg, and a bridge portion extending between a proximal end of the first leg and a proximal end of the second leg.

5. The system of claim 4, wherein the first and second legs each define a lumen extending therethrough.

6. The system of claim 5, wherein a diameter of the lumen is less than the diameter of the enlarged region of the piercing tip.

7. The system of claim 6, wherein proximal retraction of the piercing tip relative to the anchor member is configured to radially deform a distal end region of the first leg and a distal end region of the second leg.

8. The system of claim 4, wherein the first leg comprises a first pair of slots extending proximally from a distal end thereof and the second leg comprises a second pair of slots extending proximally from a distal end thereof.

9. The system of claim 4, wherein the first leg comprises a first slit extending distally from a proximal end thereof and the second leg comprises a second slit extending distally from a proximal end thereof.

10. The system of claim 4, wherein a distal end of the first leg and a distal end of the second leg are each beveled.

11. A delivery system for delivering an anchor member to a bone of a patient the system comprising:
    a bone punch including:
        an elongate shaft,
        a head at a proximal end of the elongate shaft; and
        a piercing tip at a distal end of the elongate shaft, the piercing tip including at least one piercing element having a sharpened distal end, wherein a distal end region of the at least one piercing element has an enlarged region having an outer diameter greater than an outer diameter of a proximal end region of the at least one piercing element; and
    an anchor member slidably disposed over the at least one piercing element with the sharpened distal end extending distal of the anchor member, the anchor member comprising a staple having a first leg, a second leg, and a bridge portion extending between a proximal end of the first leg and a proximal end of the second leg;
    wherein the anchor member is configured to penetrate the bone of the patient in cooperation with the piercing tip; and
    wherein proximal retraction of the piercing tip relative to the anchor member is configured to radially deform a distal end region of the first leg and radially deform a distal end region of the second leg.

12. The system of claim 11, wherein proximal translation of the piercing tip is configured to deploy the anchor member from the piercing tip.

13. The system of claim 12, wherein as the anchor member is deployed, a distal end region of the anchor member is configured to radially expand.

14. The system of claim 11, wherein the anchor member includes at least one lumen, the at least one lumen having a diameter less than the outer diameter of the enlarged region of the at least one piercing element.

15. A delivery system for delivering an anchor member to a bone of a patient, the system comprising:
    a bone punch including an elongate shaft, a head at a proximal end of the elongate shaft, and a piercing tip at a distal end of the elongate shaft, a distal end of the piercing tip including an enlarged region having a diameter greater than a diameter of a proximal end region of the piercing tip extending proximal of the enlarged region, wherein the piercing tip is configured to be driven into the bone;
    an anchor member comprising a staple having a first leg, a second leg, and a bridge portion extending between a proximal end of the first leg and a proximal end of the second leg, the first and second legs each defining a lumen extending therethrough, the anchor member disposed over at least a portion of the piercing tip with the piercing tip extending distal of the anchor member;

wherein the anchor member is configured to penetrate the bone of the patient in cooperation with the piercing tip;

wherein a diameter of the lumen is less than the diameter of the enlarged region of the piercing tip; and wherein proximal retraction of the piercing tip relative to the anchor member is configured to radially deform a distal end region of the first leg and a distal end region of the second leg.

16. The system of claim 15, wherein the first leg comprises a first pair of slots extending proximally from a distal end thereof and the second leg comprises a second pair of slots extending proximally from a distal end thereof.

17. The system of claim 15, wherein the first leg comprises a first slit extending distally from a proximal end thereof and the second leg comprises a second slit extending distally from a proximal end thereof.

18. The system of claim 15, wherein a distal end of the first leg and a distal end of the second leg are each beveled.

19. The system of claim 15, wherein the piercing tip comprises a first piercing element and a second piercing element extending parallel to the first piercing element.

* * * * *